US012575950B2

(12) United States Patent (10) Patent No.: US 12,575,950 B2
Einarsson et al. (45) Date of Patent: Mar. 17, 2026

(54) METHODS AND SYSTEMS FOR CONTROLLING A PROSTHETIC OR ORTHOTIC DEVICE

(71) Applicant: Össur Iceland ehf, Reykjavík (IS)

(72) Inventors: Árni Einarsson, Reykjavik (IS); David Langlois, Quebec (CA)

(73) Assignee: Össur Iceland ehf, Reykjavik (IS)

( * ) Notice: Subject to any disclaimer, the term of this patent is extended or adjusted under 35 U.S.C. 154(b) by 943 days.

(21) Appl. No.: 17/753,735

(22) PCT Filed: Sep. 18, 2020

(86) PCT No.: PCT/US2020/051631
§ 371 (c)(1),
(2) Date: Mar. 11, 2022

(87) PCT Pub. No.: WO2021/055851
PCT Pub. Date: Mar. 25, 2021

(65) Prior Publication Data
US 2022/0378588 A1 Dec. 1, 2022

Related U.S. Application Data

(60) Provisional application No. 62/902,103, filed on Sep. 18, 2019.

(51) Int. Cl.
*A61F 2/70* (2006.01)
*A61F 2/60* (2006.01)
(Continued)

(52) U.S. Cl.
CPC .................. *A61F 2/70* (2013.01); *A61F 2/60* (2013.01); *A61F 5/0102* (2013.01); *A61F 2002/7635* (2013.01); *A61F 2005/0188* (2013.01)

(58) Field of Classification Search
CPC ... A61F 2/70; A61F 2/74; B25J 9/0006; B25J 13/00
See application file for complete search history.

(56) References Cited

U.S. PATENT DOCUMENTS

| | | | |
|---|---|---|---|
| 909,859 | A | 1/1909 | Apgar |
| 1,289,580 | A | 12/1918 | Vincenti |
| (Continued) | | | |

FOREIGN PATENT DOCUMENTS

| | | |
|---|---|---|
| CA | 2 546 858 | 6/2005 |
| CH | 543 277 | 12/1973 |
| (Continued) | | |

OTHER PUBLICATIONS

International Search Report and Written Opinion in International Application No. PCT/US2020/051631 dated Dec. 3, 2020 in 11 pages.
(Continued)

*Primary Examiner* — Christie Bahena
(74) *Attorney, Agent, or Firm* — Knobbe, Martens, Olson & Bear, LLP

(57) ABSTRACT
A prosthetic or orthotic device (POD) can include first and second limb members coupled at a joint, an actuator, and a controller. The actuator can be configured to actuate the first limb member relative to the second limb member. The controller can cause the actuator to exhibit a force rejection behavior during a portion of stance phase and cause the actuator to exhibit a force following behavior during a portion of swing phase. The controller can, based on a determination that a gait parameter satisfies a gait parameter threshold, cause the actuator to at least one of: apply a first torque at the joint to cause the POD to flex during a portion of stance phase, decelerate flexion of the POD during at least
(Continued)

a first portion of the swing phase, or decelerate extension of the POD during at least a second portion of the swing phase.

19 Claims, 9 Drawing Sheets

(51) Int. Cl.
    *A61F 5/01*        (2006.01)
    *A61F 2/76*        (2006.01)

(56)                    References Cited

U.S. PATENT DOCUMENTS

| | | | |
|---|---|---|---|
| 2,475,373 A | 7/1949 | Catranis | |
| 2,530,286 A | 11/1950 | Catranis | |
| 2,568,051 A | 9/1951 | Catranis | |
| 3,557,387 A | 1/1971 | Ohlenbusch et al. | |
| 3,589,134 A | 6/1971 | Hackmann | |
| 3,871,032 A | 3/1975 | Karas | |
| 3,953,900 A | 5/1976 | Thompson | |
| 3,995,324 A | 12/1976 | Burch | |
| 4,030,141 A | 6/1977 | Graupe | |
| 4,172,433 A | 10/1979 | Bianchi et al. | |
| 4,209,860 A | 7/1980 | Graupe | |
| 4,387,472 A | 6/1983 | Wilson | |
| 4,488,320 A | 12/1984 | Wilson | |
| 4,579,558 A | 4/1986 | Ramer | |
| 4,652,266 A | 3/1987 | Truesdell | |
| 4,776,852 A | 10/1988 | Rubic | |
| 4,805,455 A | 2/1989 | DelGiorno et al. | |
| 5,020,790 A | 6/1991 | Beard et al. | |
| 5,062,673 A | 11/1991 | Mimura | |
| 5,101,472 A | 3/1992 | Repperger | |
| 5,116,384 A | 5/1992 | Wilson et al. | |
| 5,156,630 A | 10/1992 | Rappoport et al. | |
| 5,201,772 A | 4/1993 | Maxwell | |
| 5,246,465 A | 9/1993 | Rincoe et al. | |
| 5,252,102 A | 10/1993 | Singer et al. | |
| 5,252,901 A | 10/1993 | Ozawa et al. | |
| 5,282,460 A | 2/1994 | Boldt | |
| 5,376,138 A | 12/1994 | Bouchard et al. | |
| 5,376,141 A | 12/1994 | Phillips | |
| 5,383,939 A | 1/1995 | James | |
| 5,413,611 A | 5/1995 | Haslam, II et al. | |
| 5,425,780 A | 6/1995 | Flatt et al. | |
| 5,430,643 A | 7/1995 | Seraji | |
| 5,443,528 A | 8/1995 | Allen | |
| 5,455,497 A | 10/1995 | Hirose et al. | |
| 5,484,389 A | 1/1996 | Stark et al. | |
| 5,560,281 A | 10/1996 | Schneid | |
| 5,571,205 A | 11/1996 | James | |
| 5,650,704 A | 7/1997 | Pratt et al. | |
| 5,662,693 A | 9/1997 | Johnson et al. | |
| 5,695,527 A | 12/1997 | Allen | |
| 5,800,570 A | 9/1998 | Collier | |
| 5,888,212 A * | 3/1999 | Petrofsky | F16F 9/46 |
| | | | 623/44 |
| 5,888,213 A | 3/1999 | Sears et al. | |
| 5,893,891 A | 4/1999 | Zahedi | |
| 5,929,332 A | 7/1999 | Brown | |
| 5,948,021 A | 9/1999 | Radcliffe | |
| 5,954,621 A | 9/1999 | Joutras et al. | |
| 5,957,981 A | 9/1999 | Gramnaes | |
| 5,984,972 A | 11/1999 | Huston et al. | |
| 6,029,374 A | 2/2000 | Herr et al. | |
| 6,071,313 A | 6/2000 | Phillips | |
| 6,086,616 A | 7/2000 | Okuda et al. | |
| 6,091,977 A | 7/2000 | Tarjan et al. | |
| 6,117,177 A | 9/2000 | Chen et al. | |
| 6,122,960 A | 9/2000 | Hutchings et al. | |
| 6,129,766 A | 10/2000 | Johnson et al. | |
| 6,187,052 B1 | 2/2001 | Molino et al. | |
| 6,206,932 B1 | 3/2001 | Johnson | |
| 6,378,190 B2 | 4/2002 | Akeel | |
| 6,379,393 B1 | 4/2002 | Mavroidis et al. | |
| 6,423,098 B1 | 7/2002 | Biedermann | |
| 6,436,149 B1 | 8/2002 | Rincoe | |
| 6,443,993 B1 | 9/2002 | Koniuk | |
| 6,494,039 B2 | 12/2002 | Pratt et al. | |
| 6,500,210 B1 | 12/2002 | Sabolich et al. | |
| 6,517,585 B1 | 2/2003 | Zahedi et al. | |
| 6,517,858 B1 | 2/2003 | Le Moel et al. | |
| 6,522,266 B1 | 2/2003 | Soehren et al. | |
| 6,543,987 B2 | 4/2003 | Ehrat | |
| 6,587,728 B2 | 7/2003 | Fang et al. | |
| 6,610,101 B2 | 8/2003 | Herr et al. | |
| 6,613,097 B1 | 9/2003 | Cooper | |
| 6,645,252 B2 | 11/2003 | Asai et al. | |
| 6,679,920 B2 | 1/2004 | Biedermann et al. | |
| 6,695,885 B2 | 2/2004 | Schulman et al. | |
| 6,704,024 B2 | 3/2004 | Robotham et al. | |
| 6,704,582 B2 | 3/2004 | Le-Faucheur et al. | |
| 6,719,807 B2 | 4/2004 | Harris | |
| 6,755,870 B1 | 6/2004 | Biedermann et al. | |
| 6,761,743 B1 | 7/2004 | Johnson | |
| 6,764,520 B2 | 7/2004 | Deffenbaugh et al. | |
| 6,764,521 B2 | 7/2004 | Molino et al. | |
| 6,767,370 B1 | 7/2004 | Mosler et al. | |
| 6,813,582 B2 | 11/2004 | Levi et al. | |
| 6,824,569 B2 | 11/2004 | Okediji | |
| 6,863,695 B2 | 3/2005 | Doddroe et al. | |
| 6,875,241 B2 | 4/2005 | Christensen | |
| 6,908,488 B2 | 6/2005 | Paasivaara et al. | |
| 6,910,331 B2 | 6/2005 | Asai et al. | |
| 6,955,692 B2 | 10/2005 | Grundei | |
| 6,966,882 B2 | 11/2005 | Horst | |
| 6,969,408 B2 | 11/2005 | Lecomte et al. | |
| 7,029,500 B2 | 4/2006 | Martin | |
| 7,066,964 B2 | 6/2006 | Wild | |
| 7,112,938 B2 | 9/2006 | Takenaka et al. | |
| 7,118,601 B2 | 10/2006 | Yasui | |
| 7,137,998 B2 | 11/2006 | Bédard et al. | |
| 7,147,667 B2 | 12/2006 | Bédard et al. | |
| 7,150,762 B2 | 12/2006 | Caspers | |
| 7,164,967 B2 | 1/2007 | Etienne-Cummings et al. | |
| 7,182,738 B2 | 2/2007 | Bonutti et al. | |
| 7,209,788 B2 | 4/2007 | Nicolelis et al. | |
| 7,279,009 B2 | 10/2007 | Herr et al. | |
| 7,295,892 B2 | 11/2007 | Herr et al. | |
| 7,300,240 B2 | 11/2007 | Brogardh | |
| 7,308,333 B2 | 12/2007 | Kern et al. | |
| 7,313,463 B2 | 12/2007 | Herr et al. | |
| 7,314,490 B2 | 1/2008 | Bédard et al. | |
| 7,381,192 B2 | 6/2008 | Brodard et al. | |
| 7,396,337 B2 | 7/2008 | McBean et al. | |
| 7,410,471 B1 | 8/2008 | Campbell et al. | |
| 7,455,696 B2 | 11/2008 | Bisbee, III et al. | |
| 7,462,201 B2 | 12/2008 | Christensen | |
| 7,485,152 B2 | 2/2009 | Haynes et al. | |
| 7,520,904 B2 | 4/2009 | Christensen | |
| 7,531,006 B2 | 5/2009 | Clausen et al. | |
| 7,544,172 B2 | 6/2009 | Santos-Munne et al. | |
| 7,552,664 B2 | 6/2009 | Bulatowicz | |
| 7,575,602 B2 | 8/2009 | Amirouche et al. | |
| 7,578,799 B2 | 8/2009 | Thorsteinsson et al. | |
| 7,637,957 B2 | 12/2009 | Ragnarsdottir et al. | |
| 7,637,959 B2 | 12/2009 | Clausen et al. | |
| 7,655,050 B2 | 2/2010 | Palmer et al. | |
| 7,691,154 B2 | 4/2010 | Asgeirsson et al. | |
| 7,736,394 B2 | 6/2010 | Bédard et al. | |
| 7,799,091 B2 | 9/2010 | Herr et al. | |
| 7,811,333 B2 | 10/2010 | Jónsson et al. | |
| 7,811,334 B2 | 10/2010 | Ragnarsdottir et al. | |
| 7,815,689 B2 | 10/2010 | Bédard et al. | |
| 7,867,284 B2 | 1/2011 | Bédard et al. | |
| 7,918,808 B2 | 4/2011 | Simmons | |
| 7,942,935 B2 | 5/2011 | Iversen et al. | |
| 7,955,398 B2 | 6/2011 | Bédard et al. | |
| 7,985,265 B2 | 7/2011 | Moser et al. | |
| 7,992,849 B2 | 8/2011 | Sugar et al. | |
| 8,011,229 B2 | 9/2011 | Lieberman et al. | |
| 8,048,007 B2 | 11/2011 | Roy | |
| 8,048,172 B2 | 11/2011 | Jonsson et al. | |
| 8,057,550 B2 | 11/2011 | Clausen | |

(56)                    References Cited

U.S. PATENT DOCUMENTS

| | | | |
|---|---|---|---|
| 8,075,633 | B2 | 12/2011 | Herr et al. |
| 8,083,807 | B2 | 12/2011 | Auberger et al. |
| 8,109,890 | B2 | 2/2012 | Kamiar et al. |
| 8,142,370 | B2 | 3/2012 | Weinberg et al. |
| 8,231,687 | B2 | 7/2012 | Bédard et al. |
| 8,323,354 | B2 | 12/2012 | Bédard et al. |
| 8,403,997 | B2 | 3/2013 | Sykes et al. |
| 8,419,804 | B2 | 4/2013 | Herr et al. |
| 8,435,309 | B2 | 5/2013 | Gilbert et al. |
| 8,480,760 | B2 | 7/2013 | Hansen et al. |
| 8,500,823 | B2 | 8/2013 | Herr et al. |
| 8,512,415 | B2 | 8/2013 | Herr et al. |
| 8,551,184 | B1 | 10/2013 | Herr |
| 7,431,737 | C1 | 12/2013 | Ragnarsdottir et al. |
| 8,601,897 | B2 | 12/2013 | Lauzier et al. |
| 8,617,254 | B2 | 12/2013 | Bisbee, III et al. |
| 8,657,886 | B2 | 2/2014 | Clausen et al. |
| 8,702,811 | B2 | 4/2014 | Ragnarsdottir et al. |
| 7,896,927 | C1 | 5/2014 | Clausen et al. |
| 8,764,850 | B2 | 7/2014 | Hanset et al. |
| 8,790,282 | B2 | 7/2014 | Jung et al. |
| 8,801,802 | B2 | 8/2014 | Oddsson et al. |
| 8,814,949 | B2 | 8/2014 | Gramnaes |
| 8,852,292 | B2 | 10/2014 | Ragnarsdottir et al. |
| 8,864,846 | B2 | 10/2014 | Herr et al. |
| 8,870,967 | B2 | 10/2014 | Herr et al. |
| 8,986,397 | B2 | 3/2015 | Bédard et al. |
| 9,032,635 | B2 | 5/2015 | Herr et al. |
| 9,044,346 | B2 | 6/2015 | Langlois et al. |
| 9,060,883 | B2 | 6/2015 | Herr et al. |
| 9,060,884 | B2 | 6/2015 | Langlois |
| 9,066,819 | B2 | 6/2015 | Gramnaes |
| 9,078,774 | B2 | 7/2015 | Jónsson et al. |
| 9,114,029 | B2 | 8/2015 | Ásgeirsson |
| 9,221,177 | B2 | 12/2015 | Herr et al. |
| 9,271,851 | B2 | 3/2016 | Claussen et al. |
| 9,289,316 | B2 | 3/2016 | Ward et al. |
| 9,345,591 | B2 | 5/2016 | Bisbee, III et al. |
| 9,345,592 | B2 | 5/2016 | Herr et al. |
| 9,351,856 | B2 | 5/2016 | Herr et al. |
| 9,358,137 | B2 | 6/2016 | Bédard et al. |
| 9,459,698 | B2 | 10/2016 | Lee |
| 9,462,966 | B2 | 10/2016 | Clausen et al. |
| 9,498,401 | B2 | 11/2016 | Herr et al. |
| 9,526,635 | B2 | 12/2016 | Gilbert et al. |
| 9,526,636 | B2 | 12/2016 | Bédard et al. |
| 9,532,877 | B2 | 1/2017 | Holgate |
| 9,554,922 | B2 | 1/2017 | Casler et al. |
| 9,561,118 | B2 | 2/2017 | Clausen et al. |
| 9,604,368 | B2 | 3/2017 | Holgate |
| 9,622,884 | B2 | 4/2017 | Holgate et al. |
| 9,649,206 | B2 | 5/2017 | Bédard |
| 9,682,005 | B2 | 6/2017 | Herr et al. |
| 9,687,377 | B2 | 6/2017 | Han et al. |
| 9,707,104 | B2 | 7/2017 | Clausen |
| 9,717,606 | B2 | 8/2017 | Gramnaes |
| 9,737,419 | B2 | 8/2017 | Herr et al. |
| 9,808,357 | B2 | 11/2017 | Langlois |
| 9,839,552 | B2 | 12/2017 | Han et al. |
| 9,895,240 | B2 | 2/2018 | Langlois et al. |
| 10,195,057 | B2 | 2/2019 | Clausen |
| 10,251,762 | B2 | 4/2019 | Langlois |
| 10,299,943 | B2 | 5/2019 | Clausen et al. |
| 10,307,271 | B2 | 6/2019 | Holgate et al. |
| 10,369,019 | B2 | 8/2019 | Clausen et al. |
| 10,390,974 | B2 | 8/2019 | Clausen et al. |
| 10,405,996 | B2 | 9/2019 | Langlois |
| 10,543,109 | B2 | 1/2020 | Holgate |
| 10,575,970 | B2 | 3/2020 | Holgate |
| 10,695,197 | B2 | 6/2020 | Clausen |
| 10,940,027 | B2 | 3/2021 | Langlois et al. |
| 11,007,072 | B2 | 5/2021 | Gilbert et al. |
| 11,185,429 | B2 | 11/2021 | Langlois |
| 11,285,024 | B2 | 3/2022 | Clausen et al. |
| 11,446,166 | B2 | 9/2022 | Clausen et al. |
| 11,576,795 | B2 | 2/2023 | Clausen |
| 11,607,326 | B2 | 3/2023 | Langlois |
| 2002/0007690 | A1 | 1/2002 | Song et al. |
| 2002/0040601 | A1 | 4/2002 | Fyfe et al. |
| 2002/0079857 | A1 | 6/2002 | Ishii et al. |
| 2003/0005786 | A1 | 1/2003 | Stuart et al. |
| 2004/0064195 | A1 | 4/2004 | Herr |
| 2004/0078299 | A1 | 4/2004 | Down-Logan et al. |
| 2004/0153484 | A1 | 8/2004 | Unno |
| 2004/0169112 | A1 | 9/2004 | Grossart |
| 2005/0049719 | A1 | 3/2005 | Wilson |
| 2005/0049721 | A1 | 3/2005 | Sulprizio |
| 2005/0070834 | A1 | 3/2005 | Herr et al. |
| 2005/0107889 | A1 | 5/2005 | Bédard et al. |
| 2005/0113973 | A1 | 5/2005 | Endo et al. |
| 2005/0137717 | A1 | 6/2005 | Gramnaes |
| 2005/0166685 | A1 | 8/2005 | Boiten |
| 2005/0216097 | A1 | 9/2005 | Rifkin |
| 2005/0251079 | A1 | 11/2005 | Carvey et al. |
| 2005/0283257 | A1 | 12/2005 | Bisbee et al. |
| 2006/0025959 | A1 | 2/2006 | Gomez et al. |
| 2006/0069336 | A1 | 3/2006 | Krebs et al. |
| 2006/0069448 | A1 | 3/2006 | Yasui |
| 2006/0184280 | A1 | 8/2006 | Oddsson et al. |
| 2006/0189899 | A1 | 8/2006 | Flaherty et al. |
| 2006/0224247 | A1 | 10/2006 | Clausen et al. |
| 2006/0249315 | A1 | 11/2006 | Herr et al. |
| 2006/0259153 | A1 | 11/2006 | Harn et al. |
| 2006/0260620 | A1 | 11/2006 | Kazerooni et al. |
| 2007/0043449 | A1 | 2/2007 | Herr et al. |
| 2007/0061016 | A1 | 3/2007 | Kuo et al. |
| 2007/0123997 | A1 | 5/2007 | Herr et al. |
| 2007/0129653 | A1 | 6/2007 | Sugar et al. |
| 2007/0162152 | A1 | 7/2007 | Herr et al. |
| 2008/0004718 | A1 | 1/2008 | Mosler |
| 2008/0046096 | A1 | 2/2008 | Bédard et al. |
| 2008/0058668 | A1 | 3/2008 | Seyed Momen et al. |
| 2008/0141813 | A1 | 6/2008 | Ehrat |
| 2008/0262635 | A1 | 10/2008 | Moser et al. |
| 2008/0306612 | A1 | 12/2008 | Mosler |
| 2009/0030530 | A1 | 1/2009 | Martin |
| 2009/0082869 | A1 | 3/2009 | Slemker et al. |
| 2009/0088912 | A1 | 4/2009 | Rajaraman |
| 2009/0192625 | A1 | 7/2009 | Boiten |
| 2009/0204229 | A1 | 8/2009 | Mosley et al. |
| 2009/0204230 | A1 | 8/2009 | Kaltenborn et al. |
| 2009/0265018 | A1 | 10/2009 | Goldfarb et al. |
| 2010/0023133 | A1 | 1/2010 | Fairbanks et al. |
| 2010/0042228 | A1 | 2/2010 | Doddroe et al. |
| 2010/0094431 | A1 | 4/2010 | Albrecht-Laatsch |
| 2010/0113980 | A1 | 5/2010 | Herr et al. |
| 2010/0114329 | A1 | 5/2010 | Casler et al. |
| 2010/0131101 | A1 | 5/2010 | Engeberg et al. |
| 2010/0161077 | A1 | 6/2010 | Boone et al. |
| 2010/0174384 | A1 | 7/2010 | Herr et al. |
| 2010/0185301 | A1 | 7/2010 | Hansen et al. |
| 2010/0241242 | A1 | 9/2010 | Herr et al. |
| 2010/0275718 | A1 | 11/2010 | Stuart et al. |
| 2010/0305716 | A1 | 12/2010 | Pusch et al. |
| 2011/0015761 | A1 | 1/2011 | Celebi et al. |
| 2011/0082566 | A1 | 4/2011 | Herr et al. |
| 2011/0106274 | A1 | 5/2011 | Ragnarsdottir et al. |
| 2011/0132131 | A1 | 6/2011 | Worz |
| 2011/0137429 | A1 | 6/2011 | Bédard et al. |
| 2011/0166674 | A1 | 7/2011 | Montmartin |
| 2011/0196509 | A1 | 8/2011 | Jansen et al. |
| 2011/0202144 | A1 | 8/2011 | Palmer et al. |
| 2011/0208322 | A1 | 8/2011 | Rifkin et al. |
| 2011/0295384 | A1 | 12/2011 | Herr et al. |
| 2011/0295385 | A1 | 12/2011 | Herr et al. |
| 2012/0078415 | A1 | 3/2012 | Kubo et al. |
| 2012/0130508 | A1 | 5/2012 | Harris et al. |
| 2012/0185052 | A1 | 7/2012 | Lefeber |
| 2012/0203359 | A1 | 8/2012 | Schimmels et al. |
| 2012/0209405 | A1 | 8/2012 | Herr et al. |
| 2012/0226364 | A1 | 9/2012 | Kampas et al. |
| 2012/0259430 | A1 | 10/2012 | Han et al. |
| 2012/0283845 | A1 | 11/2012 | Herr et al. |
| 2012/0330439 | A1 | 12/2012 | Goldfarb et al. |

(56)                    References Cited

U.S. PATENT DOCUMENTS

| | | | |
|---|---|---|---|
| 2013/0035769 A1 | 2/2013 | Bédard et al. | |
| 2013/0142608 A1 | 6/2013 | Zhang et al. | |
| 2013/0173022 A1 | 7/2013 | Arabian et al. | |
| 2013/0197408 A1 | 8/2013 | Goldfarb et al. | |
| 2013/0218295 A1 | 8/2013 | Holgate et al. | |
| 2013/0218298 A1 | 8/2013 | Mosler | |
| 2013/0261766 A1* | 10/2013 | Langlois | A61F 2/70 |
| | | | 623/33 |
| 2013/0282141 A1 | 10/2013 | Herr et al. | |
| 2013/0310949 A1* | 11/2013 | Goldfarb | A61F 2/60 |
| | | | 623/27 |
| 2014/0039642 A1 | 2/2014 | Nijiman et al. | |
| 2014/0114437 A1 | 4/2014 | Herr et al. | |
| 2014/0121782 A1 | 5/2014 | Herr et al. | |
| 2014/0191522 A1 | 7/2014 | Birglen | |
| 2015/0032225 A1 | 1/2015 | Oddsson et al. | |
| 2015/0073566 A1 | 3/2015 | Ragnarsdottir et al. | |
| 2015/0099253 A1* | 4/2015 | De Roy | A61F 2/64 |
| | | | 434/274 |
| 2015/0127118 A1 | 5/2015 | Herr et al. | |
| 2015/0164661 A1 | 6/2015 | Ragnarsdottir et al. | |
| 2015/0209214 A1 | 7/2015 | Herr et al. | |
| 2015/0265429 A1 | 9/2015 | Jónsson et al. | |
| 2016/0158031 A1 | 6/2016 | Ward et al. | |
| 2016/0158032 A1 | 6/2016 | Ward et al. | |
| 2016/0296346 A1* | 10/2016 | Burke | A61F 2/68 |
| 2017/0049659 A1 | 2/2017 | Farris et al. | |
| 2017/0241497 A1 | 8/2017 | Mooney et al. | |
| 2017/0340504 A1 | 11/2017 | Sanz Merodio et al. | |
| 2019/0224026 A1 | 7/2019 | Clausen et al. | |
| 2019/0365545 A1 | 12/2019 | Langlois | |
| 2020/0000611 A1 | 1/2020 | Clausen et al. | |
| 2020/0214856 A1 | 7/2020 | Hogate | |
| 2020/0383804 A1 | 12/2020 | Clausen | |
| 2022/0249260 A1 | 8/2022 | Clausen et al. | |
| 2023/0064710 A1 | 3/2023 | Clausen et al. | |

FOREIGN PATENT DOCUMENTS

| | | | | | |
|---|---|---|---|---|---|
| CN | 2043873 U | 9/1989 | | | |
| CN | 1215614 | 5/1999 | | | |
| CN | 2400072 Y | 10/2000 | | | |
| CN | 2776340 | 5/2006 | | | |
| DE | 39 23 057 | 1/1991 | | | |
| DE | 42 29 330 | 3/1994 | | | |
| DE | 197 54 690 | 7/1999 | | | |
| EP | 0 358 056 | 3/1990 | | | |
| EP | 0 380 060 | 8/1990 | | | |
| EP | 0 549 855 | 7/1993 | | | |
| EP | 0 718 951 | 6/1996 | | | |
| EP | 1 107 420 | 6/2001 | | | |
| EP | 1 169 982 | 1/2002 | | | |
| EP | 1 410 780 | 4/2004 | | | |
| EP | 1 442 704 | 8/2004 | | | |
| EP | 1 547 567 | 6/2005 | | | |
| EP | 1 792 597 | 6/2007 | | | |
| EP | 2 257 247 | 12/2010 | | | |
| EP | 2 702 963 | 3/2014 | | | |
| FR | 2 816 463 | 5/2002 | | | |
| GB | 628958 | 9/1949 | | | |
| GB | 2 201 260 | 8/1988 | | | |
| GB | 2 228 201 | 8/1990 | | | |
| GB | 2 260 495 | 4/1993 | | | |
| GB | 2 301 776 | 12/1996 | | | |
| GB | 2 302 949 | 2/1997 | | | |
| GB | 2 367 753 | 4/2002 | | | |
| JP | 59-032453 | 2/1984 | | | |
| JP | 59-071747 | 4/1984 | | | |
| JP | 59-088147 | 5/1984 | | | |
| JP | 59-189843 | 10/1984 | | | |
| JP | 60-177102 | 9/1985 | | | |
| JP | 05-123348 | 5/1993 | | | |
| JP | 05-161668 | 6/1993 | | | |
| JP | 07-024766 | 1/1995 | | | |
| JP | 11-215793 | 8/1999 | | | |
| JP | 2002-191654 | 7/2002 | | | |
| JP | 2002-219141 | 8/2002 | | | |
| JP | 2002-533161 | 10/2002 | | | |
| JP | 2005-536317 | 12/2005 | | | |
| JP | 2009-153660 | 7/2009 | | | |
| JP | 05-128132 | 1/2013 | | | |
| KR | 2002-0041137 | 6/2002 | | | |
| SU | 1447366 | 12/1988 | | | |
| SU | 1731210 | 5/1992 | | | |
| WO | WO 94/009727 | 5/1994 | | | |
| WO | WO 96/025898 | 8/1996 | | | |
| WO | WO 96/041599 | 12/1996 | | | |
| WO | WO 97/000661 | 1/1997 | | | |
| WO | WO 97/027822 | 8/1997 | | | |
| WO | WO 98/025552 | 6/1998 | | | |
| WO | WO 99/029272 | 6/1999 | | | |
| WO | WO 00/027318 | 5/2000 | | | |
| WO | WO 00/030572 | 6/2000 | | | |
| WO | WO 00/038599 | 7/2000 | | | |
| WO | WO 01/006965 | 2/2001 | | | |
| WO | WO 03/003953 | 1/2003 | | | |
| WO | WO 03/088373 | 10/2003 | | | |
| WO | WO 2004/017890 | 3/2004 | | | |
| WO | WO 2006/024876 | 3/2006 | | | |
| WO | WO 2006/076164 | 7/2006 | | | |
| WO | WO-2006112774 A1 * | 10/2006 | | A61F 2/6607 | |
| WO | WO 2007/025116 | 3/2007 | | | |
| WO | WO 2007/095933 | 8/2007 | | | |
| WO | WO-2008086629 A1 * | 7/2008 | | A61F 2/60 | |
| WO | WO 2010/004217 | 1/2010 | | | |
| WO | WO 2010/027968 | 3/2010 | | | |
| WO | WO 2011/005482 | 1/2011 | | | |
| WO | WO 2011/096965 | 8/2011 | | | |
| WO | WO 2012/062279 | 5/2012 | | | |
| WO | WO 2012/091555 | 7/2012 | | | |
| WO | WO 2013/006585 | 1/2013 | | | |
| WO | WO-2013088142 A1 * | 6/2013 | | A61F 2/70 | |
| WO | WO 2015/157723 | 10/2015 | | | |
| WO | WO 2019/148021 | 8/2019 | | | |
| WO | WO 2021/055851 | 3/2021 | | | |

OTHER PUBLICATIONS

International Preliminary Report on Patentability and Written Opinion in International Application No. PCT/US2020/051631 dated Mar. 31, 2022 in 8 pages.
Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.
Dietl et al., "Der Einsatz von Elektronik bei Prothesen zur Versorgung der unteren Extremität," Med. Orth. Tech., 1997, vol. 117, pp. 31-35.
Diginfo TV, "Powered Prosthetic Thigh and Leg", uploaded Nov. 7, 2008 http://www.youtube.com/watch?v=igitTzNEd54&feature=youtu.be%3E [Screenshots retrieved Oct. 23, 2014 in 9 pages].
"Extension Spring Design Theory, Spring Rate of Extension Springs," http://web.archive.org/web/2013120912508/http://springpedia.com/extension-design-theory.asp as archived Dec. 9, 2013 in 1 page.
Flowers et al., "An Electrohydraulic Knee—Torque Controller for a Prosthesis Simulator," Journal of Biomechanical Engineering: Transactions of the ASME; vol. 99, Series K, No. 1; Feb. 1977, pp. 3-8.
Herr et al., "Patient-Adaptive Prosthetic and Orthotic Leg Systems," In Proceedings of the 12th Nordic Baltic Conference on Biomedical Engineering and Medical Physics, Jun. 18-22, 2002, pp. 18-21.
Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.
Robinson et al., "Series Elastic Actuator Development for a Biomimetic Walking Robot," MIT Leg Laboratory, 1999, pp. 1-8.

(56)           References Cited

OTHER PUBLICATIONS

Townsend et al., "Biomechanics and Modeling of Bipedal Climbing and Descending," Journal of Biomechanics, vol. 9, No. 4, 1976, pp. 227-239.

* cited by examiner

900

METHODS AND SYSTEMS FOR CONTROLLING A PROSTHETIC OR ORTHOTIC DEVICE

RELATED APPLICATIONS

The present application is a U.S. National Phase of International App. No. PCT/US2020/051631, entitled "METHODS AND SYSTEMS FOR CONTROLLING A PROSTHETIC OR ORTHOTIC DEVICE," filed Sep. 18, 2020, and which claims priority to U.S. Provisional App. No. 62/902,103 filed Sep. 18, 2019. Both International App. No. PCT/US2020/051631 and U.S. Provisional App. No. 62/902,103 are hereby incorporated herein by reference in their entirety.

TECHNICAL FIELD

The present disclosure is related to prosthetic or orthotic systems, in particular to motorized prosthetic or orthotic devices (PODs) and control systems and methods for operating the same.

BACKGROUND

Over the years, many kinds of PODs have been devised in an effort to replace the limbs that amputees have lost. In particular, efforts have been made to develop PODs that will replace the loss of major limbs, such as legs and arms, in view of the immense impact that such a loss has on the amputee. All these PODs have the difficult task of giving to these amputees as normal of a life as possible. The task is particularly difficult for leg prostheses due in part to the complexity of human locomotion.

In some cases, mechanical linkages and braking systems can reproduce at least some of the basic behaviors of the human knee, such as locking the knee during stance phase or freely swinging the knee during aerial or swing phase. However, these systems can be unable to sustain yielding behaviors, such as those desired when going down a set of stairs or sitting down. In some cases, the foregoing yielding management problems can be resolved using more advanced mechanical features or using hydraulic systems. However, even these more advanced systems are generally unable to generate motion of the joint, but for by very basic mechanical means such as a spring.

To that end, battery powered electric motors or actuators have been incorporated into some PODs to facilitate the amputee's gait cycle.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

DETAILED DESCRIPTION

Figure 1:
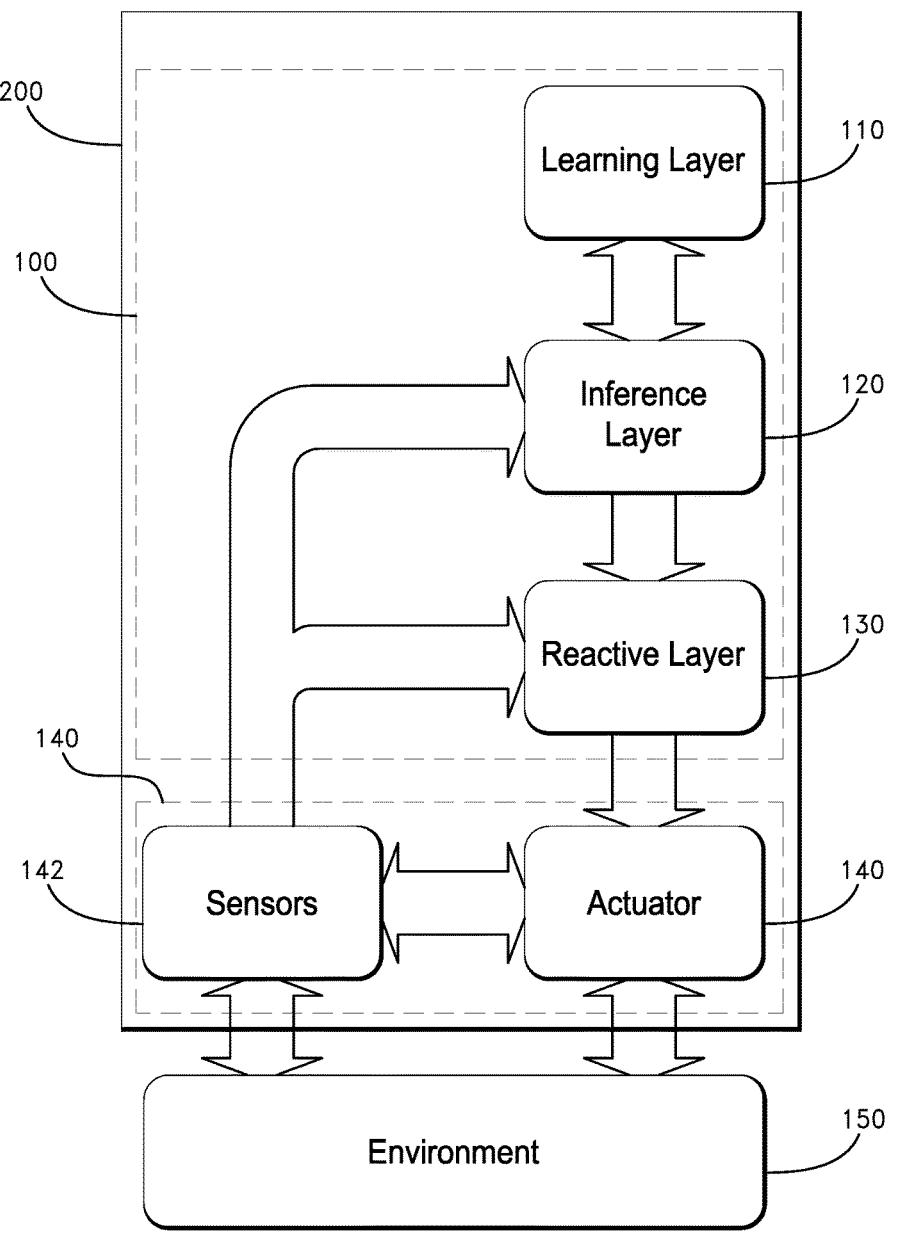
FIG. 1 is a block diagram of the interaction between various controls system layers and building blocks of an active or semi-active POD.

An active POD (e.g., motor-powered POD) can restore some or all of the physiological behaviors of the human knee. This is made possible due at least in part to the active POD's capacity to manage both positive and negative power exchanges with the user or the environment. For example, an active POD can include an actuator that forms or is connected to a joint, and the active POD can mimic behaviors of the human knee by accelerating or decelerating actuation of the actuator at specific portions of the gait cycle, thereby facilitating flexion, extension, or stiffening of the prosthetic knee. A semi-active POD (e.g., electronically-controlled POD that provides some resistive braking effect, like a magnetorheological POD), can similarly restore some of the physiological behaviors of the human knee by managing movement of the POD (e.g., providing a resistive braking effect during different portions of gait).

Such schemes of providing an "actively modified joint behavior" (e.g., modifying the natural behavior of the POD joint, for example, by applying a torque or braking effect at particular times during portions of stance or swing phase) to a user of an active or semi-active POD can advantageously reduce the amount of energy required by the user to perform particular activities (for example, cyclical walking). However, in some instances, an active or semi-active POD may be too proactive in providing the actively modified joint behavior. For example, in activities or gait phases where little functional benefits arise from the additional power injection (for example, a transition from standing or confined ambulation towards cyclical walking), an actively modified joint behavior from an active POD may startle the user, cause the user's POD to buckle, cause a user to become unbalanced or unstable, etc. Similarly, too much braking by a semi-active POD may inhibit the gait dynamics of a user.

On the other hand, for activities or gait phases where little functional benefits arise from the additional power injection, non-powered and/or non-controlled PODs (sometimes referred to as passive PODs) can provide stable stance support or allow for a consistent transition from a relatively static position to a relatively active position. Thus, in at least some activities or gait phases, characteristics of a passive POD can be favorable to those of an active or semi-active POD.

To improve the usability and functionality of active and semi-active PODs, a hybrid control scheme can be used. The hybrid control scheme can provide flexible and dynamic phases between discrete controller states, thereby smoothing the transition between discreet activities (e.g., standing and walking). For example, within a particular activity or before transitioning from one activity to another activity, the hybrid control scheme can include one or more sub-spaces in which a passive mode is implemented and one or more different sub-spaces in which an active mode is implemented. Based on the different modes, the POD can provide different functionality to the user. For example, in the active mode, the POD may provide one or more actively modified joint behaviors and/or vary the power levels of one or more actively modified joint behaviors, whereas, in the passive mode, the POD may not provide actively modified joint behaviors to a user and/or may not vary the power levels of an actively modified joint behavior. By providing different modes, different actively modified joint behaviors, and/or different power levels of actively modified joint behaviors within the same activity (or before transitioning from one activity to another), the hybrid control scheme can smooth the transition between discreet activities (e.g., standing and walking) in a physiologically compliant way.

As a non-limiting example, in passive mode, the controller can cause the active or semi-active POD to mimic or correspond to a passive POD by providing little to no actively modified joint behavior to the user. In contrast, in active mode, the controller can cause the active or semi-active POD to function as an active POD by providing one or more actively modified joint behaviors to the user. In some cases, in active mode, the controller can cause the active POD to dynamically implement one or more types of actively modified joint behavior (e.g., toe-off assist behavior, braking behavior, bumper avoidance behavior) or dynamically modify an amount of power supplied for a particular type of actively modified joint behavior as the user transitions towards cyclical walking and/or increases a walking speed.

Passive Mode

In the passive mode, the controller (e.g., using the reactive layer) can communicate a command signal to cause the actuator to exhibit a force rejection (FR) behavior. The FR behavior can correspond to the actuator adjusting (e.g., increasing) its resistance to motion, for example by applying a torque to the joint. In some cases, the FR behavior can correspond to the actuator actively stiffening the joint segment of the POD to prevent flexion of the POD at the joint (e.g., prevent flexion of a first limb member relative to a second limb member). In certain embodiments, the actuator can stiffen the joint segment by applying a torque to the joint segment in the opposite direction of a measured torque at the joint. In certain cases, the torque applied by the actuator can equal the measured torque at the joint.

In some cases, a feedback signal is utilized to define the actuator effort when exhibiting the FR behavior. For example, the actuator's resistance to motion can be dynamically modified to oppose a force applied to the POD by the user. In this way, FR behavior can result in a locked joint (e.g., knee, ankle, etc.), independent of the amount of weight placed on it. For example, increases in torque on the knee from the user can be met with an increased torque in the opposite direction from the actuator. In some cases, to cause the actuator to exhibit FR behavior, the controller causes the actuator to apply a particular amount of torque in a particular direction. For example, the controller can determine an amount of torque at the joint segment and can cause the actuator to apply an equal or approximately equal amount of torque in the opposite direction.

In the passive mode, the controller can cause the actuator to exhibit the FR behavior during the stance phase of the user's gait cycle. For example, the controller can cause the actuator to exhibit the FR behavior during the entirety of the stance phase or during a portion of the stance phase.

In the passive mode, the controller can communicate a command signal to cause the actuator to exhibit a force following (FF) behavior. The FF behavior can correspond to the actuator adjusting (e.g., decreasing) its resistance to motion, for example by applying a torque to the joint. In some cases, the FF behavior can correspond to the actuator adjusting its resistance to motion to follow a measured torque at the joint. The measured torque may vary based at least in part on a forward motion of the joint. For example, the FF behavior can correspond to the actuator applying a torque to the joint in the same direction as a torque applied by the user or by removing torque or resistance in the joint. In this way, the actuator can cause the joint of the POD to move like a free-swinging hinge in response to torque applied to the joint by the user. In some cases, the FF behavior can correspond to the actuator applying torque to overcome an internal resistance of the joint itself. For example, the controller can cause the actuator to apply a second torque to the joint that corresponds to a torque required to overcome an internal resistance of the prosthetic. In this way, the actuator can reduce resistance caused by the joint and allow the joint to move more freely.

In some cases, a feedback signal is utilized to define the actuator effort when exhibiting the FF behavior. For example, the controller can determine a first torque applied to the joint by the user and cause the actuator to apply a second torque to the joint in the same or a similar direction as the first torque. In some cases, the second torque is equal or substantially equal to the first torque. In some cases, the second torque is equal to the sum of the first torque and a third torque. The third torque can correspond to a torque required to overcome an internal resistance of the joint itself. As an example, to cause the actuator to exhibit the FF behavior, the controller can determine a knee torque using a torque sensor and can control the actuator to apply that same amount of torque with additional torque to overcome the internal resistance of the prosthetic to the joint in the same or a substantially similar direction. In some cases, the determined knee torque can be the result of the user swinging their POD forward as part of taking a forward step.

In the passive mode, the controller can cause the actuator to exhibit the FF behavior during the swing phase of the user's gait cycle. For example, the controller cause the actuator to exhibit the FF behavior during the entirety of the swing phase or during a portion of the swing phase. In the passive mode, the controller may not cause the actuator to exhibit one or more of the toe-off assist behavior, braking behavior, or a bumper avoidance behavior, as described herein with respect to the active mode.

Active Mode

In active mode, the controller causes the actuator to implement various types of actively modified joint behavior (e.g., toe-off assist behavior, braking behavior, and bumper avoidance behavior). In some cases, the controller causes the actuator to systematically activate actively modified joint behavior features. For example, at initial activation of active mode, the controller may cause the actuator to implement all or only a subset of potential actively modified joint behavior features, such as braking behavior and/or bumper avoidance behavior (e.g., but not toe-off assist behavior). In some such cases, as the user continues to transition towards full dynamic walking, the controller may cause the actuator to implement additional actively modified joint behavior features (e.g., toe-off assist behavior). In some cases, once an actively modified joint behavior feature is activated, the controller can cause the actuator to increase a level of the actively modified joint behavior features over time. For example, in the event the controller activates all actively modified joint behavior features when transitioning to active mode, it can activate some or all of the actively modified joint behavior features at 25% capacity and then increase the power level as the user continues to transition to full dynamic walking. The power level can increase linearly (e.g., in proportion to a gait parameter) and/or in a step-wise fashion (e.g., as the gait parameter satisfies different thresholds, the power level could increase by steps of 10%, 25%, etc.). In some cases, some actively modified joint behavior features may be activated to 100% and others may scale up. For example, the braking behavior and bumper avoidance behavior may be activated to 100%, whereas the toe-off assist behavior may be activated to 25% and ramp up to 100% as the user continues to transition to a particular activity, such as full dynamic walking In the active mode, the controller (e.g., using the reactive layer) can communicate a command signal to cause the actuator exhibit FR behavior, FF behavior, and one or more types of actively modified joint behavior, such as a toe-off assist behavior, a braking behavior, and/or a bumper avoidance behavior. In the active mode, the controller can cause the actuator to exhibit the FR behavior and the toe-off assist behavior during stance phase. For example, the controller can cause the actuator to exhibit the FR behavior during a portion of the stance phase, such as between foot-strike and midstance, and can cause the actuator to exhibit the toe-off assist behavior during a portion of the stance phase, such as between midstance and toe-off. The toe-off assist behavior (or toe-off assist behavior) can correspond to the actuator applying a torque to the joint to accelerate flexion of the knee. For example, the toe-off assist behavior can correspond to the actuator causing the joint to flex.

Furthermore, in the active mode, the controller can cause the actuator to exhibit a FF behavior, a braking behavior, and/or a bumper avoidance behavior during swing phase. For example, the controller can cause the actuator to exhibit the FF behavior between toe-off and a first heel rise target, exhibit the braking behavior between the first heel rise target and a second heel rise target, exhibit the FF behavior between the second heel rise target and a first knee extension target, and/or exhibit the bumper avoidance behavior between the first extension target and a second extension target. The braking behavior can correspond to the actuator applying a torque to the joint to decelerate flexion of the knee. The bumper avoidance behavior can correspond to the actuator applying a torque to the joint to decelerate extension of the knee.

In some cases, in active mode, the controller causes the actuator to dynamically control actively modified joint behavior features. For example, in some cases, the controller can cause the actuator to exhibit only a subset of the toe-off assist behavior, the braking behavior, and the bumper avoidance behavior. As another example, the controller can cause the actuator to tune the power associated with one or more of the toe-off assist behavior, the braking behavior, or the bumper avoidance behavior.

Mode Selection

As part of a hybrid control scheme, the controller can select its controller mode (e.g., passive or active), activate one or more actively modified joint behaviors, and/or modify power levels of actively modified joint behaviors based on one or more gait parameters. For example, the controller can select the passive mode for the controller (or not activate any actively modified joint behaviors, use a limited number of actively modified joint behaviors, or not alter power levels of actively modified joint behaviors) when a gait parameter does not satisfy a first gait parameter threshold and can select the active mode for the controller (or activate one or more actively modified joint behaviors or alter power levels of actively modified joint behaviors) when one or more gait parameters satisfies one or more first gait parameter thresholds. Furthermore, in active mode, the controller can activate additional actively modified joint behaviors or increase the power level for certain types of actively modified joint behaviors when the one or more gait parameters satisfy one or more (additional) thresholds, such as a second gait parameter threshold or third gait parameter threshold.

For example, based on a gait parameter satisfying a threshold (e.g., cadence of 80 steps/minute for at least two steps), the controller can transition from a passive mode to an active mode and/or activate one or more actively modified joint behaviors. Furthermore, as the gait parameter satisfies additional thresholds (e.g., cadence of 90 steps/minute, cadence of 100 steps/minute) or the activity becomes more demanding, the controller can activate or enhance certain types of actively modified joint behavior. For example, the controller may initiate braking behavior, bumper avoidance behavior, and toe-off assist behavior at 25% capacity upon entering the active mode and then increase the percentage capacity as the gait parameter increases or satisfies additional gait parameter thresholds or the activity becomes more demanding (e.g., faster walking). As another example, the controller may initiate braking behavior, bumper avoidance behavior (but not toe-off assist behavior) upon entering the active mode, and then add toe-off assist behavior as the gait parameter increases or satisfies additional gait parameter thresholds or the activity becomes more demanding (e.g., faster walking). In certain cases, the controller can select its controller mode and/or activate one or more actively modified joint behaviors based on a combination of two or more gait parameters. For example, the controller may select a passive mode or active mode based on a duration of a stance phase and cadence or based on an absolute thigh angle at toe-off and shank sagittal plane rotational speed amplitude.

Use of such a hybrid control scheme where the basic dynamic behavior of the POD is modified during operation provides support to the user that is more efficient and more applicable to a wider range of activities than other control schemes. Additionally, using such a hybrid control scheme allows the POD to minimize the negative effects associated with passive- and active-type system behaviors or operational characteristics. For example, the actuator of an active POD can be controlled to dynamically vary between an active mode and a passive mode. The POD can transition from one mode to another mode based on a change in the user activity, such as a transition from standing to walking or walking to standing, and/or based on one or more gait parameters, as described herein.

In certain cases, the controller can select its controller mode based on a determined activity of the user and/or POD. For example, the controller can select a passive mode based on a determination that the user is standing and select an active mode based on a determination that the user is walking. In some such cases, as the user transitions from a standing activity to a slow walking activity, the controller can transition from the passive mode to the active mode. In some such cases, as the user transitions from a slow walking activity to a standing activity, the controller can transition from the active mode to the passive mode.

Gait Cycle

For sake of description, various references to a gait cycle are used. Each gait cycle can have two phases: Stance Phase and Swing Phase.

During the stance phase, the foot contacts the ground, the mass of the body is supported, and then the body is propelled forward during the later stages of stance. In general, stance phase includes five events: (i) foot strike, (ii) foot-flat, (iii) midstance, (iv) heel-off, and (v) toe-off. Foot strike is the beginning instant of the gait cycle and is represented as initial contact of one foot with the ground. Foot-flat is the instant that the rest of the foot comes down to contact the ground and usually is where full body weight is being supported by the leg. Midstance can be when the center of mass is directly above the ankle joint center or the instant when the hip joint center is above the ankle joint. Heel-off occurs when the heel begins to lift off the ground in preparation for the forward propulsion of the body. Toe-off happens as the last event of contact during the stance phase.

During the swing phase, the foot is not in contact with the ground. In general, swing phase includes three events 1) initial swing, 2) mid swing, and 3) terminal swing. During initial swing, the increased knee flexion lifts the foot/heel for toe clearance, the heel reaches a maximum heel rise (generally at the maximum flexion of the knee), and hip flexion advances the limb. During mid swing, the knee is allowed to extend and swing forward. The phase ends when the swinging limb is forward and the tibia is vertical (e.g., hip and knee flexion postures are equal). During terminal swing, limb advancement is completed by knee extension and ends when the foot or heel strikes the floor.

Control System Layering

Certain examples described herein possess the organization of the control system of a POD 100, as presented in FIG. 1. This organization of software processes, data streams, and a priori knowledge is referred to herein as a multi-layer hierarchical architecture. This method of architectural organization can satisfy at least two objectives, namely provide high performance control of an active POD, and efficiently organize processes and data stream(s) such that information received from the POD's sensors propagates through the system in an orderly and logical fashion.

The learning layer 110, the inference layer 120, and the reactive layer 130 in FIG. 1 depict the hierarchical layering of the control system architecture 105 of an active POD 100. Moreover, the sensors 142, actuator 144, and environment 150 highlight the interactions between the control system 105 and the environment in which the POD 100 operates.

In certain embodiments, the system is organized into hierarchical layers based on an examination of the flow of data into and out of the layers, as well as the interdependencies between layers. The layer names, data abstraction models, and nature of the data stream associated with certain embodiments are described herein using physiological terms. The three layers that can be used to sustain active POD operation in certain embodiments include, but are not limited to, a learning layer 110, an inference layer 120, and a reactive layer 130. The different layers can be categorized based on the level of abstraction, the time frame in which they act, etc.

The various layers interact with each other to improve the performance of the POD 100. For example, a well-tuned POD may provide reasonable performance using only the reactive 130 and inference layers 120, but may be unable to evolve in order to meet the user's changing needs, or respond to long term changes in the operating environment without the use of a learning layer 110.

The learning layer 110 can include the control structure's highest abstraction level, and can be the level furthest away from raw sensor data. The learning layer 110 can be loosely analogized to human cognitive functions, and it can be used to recursively improve the POD control system's performance as time passes. In addition, the learning layer 110 can have the longest time frame in which it acts. For example, in certain embodiments, the learning layer 110 does not respond to changes in gait pattern between steps. Rather, the leaning layer identifies and responds to long-term trends in user performance.

The learning layer 110 can also define what is considered an improvement in performance. The criteria for improved or reduced performance can evolve with time as the user becomes more familiar with the POD and demands a higher level of performance. The evolution of what optimality means can be thought of as the POD's transition from a POD possessing a moderate level of performance coupled with a very high level of safety to a POD possessing a high level of performance coupled with reduced user safety constraints, thereby increasing the POD's flexibility and performance potential. As it evolves, the learning layer 110 can also decide to allow user access to features that had previously been hidden or were not made available.

In certain embodiments, the learning layer 110 can include an expert system consisting of rule and data sets that can make decisions as to how well the POD performs in particular situations, and use the inference layer 120 to implement the high-level decision making. The learning layer 110 alters the rule set or parameter values used by the inference layer 120 incrementally and over longer periods of time to dictate POD performance.

In addition, the learning layer 110 can provide support as the controller formulation itself may sometimes require change. For example, a single actuated POD can potentially cover a large and diversified range of locomotion activities and the user can progressively adapt its behavior, which may require additional adjustment to ensure that the system maintains a stable level of performance.

The inference layer 120 can be responsible for a variety of different activities. These activities can include, but are not limited to, identifying the current activity or gait phase being performed by the user, measuring the performance of the POD 100, requesting that the learning layer 110 examine a particular performance issue, organizing and passing the requested/required data to the learning layer 110, providing the reactive layer 130 with enough data to smoothly execute the task at hand, selecting active mode or passive mode, etc.

Within the control system 105, the inference layer's role can be conceived of as mimicking the human brain's conscious decision-making process. Using the rules and data it acquires from the learning layer 110, the inference layer 120 can infer which course of action is appropriate from sensory data measurements and estimates. Thus, the inference layer 120 can mimic the human ability to apply what one has learned to specific present and future situations.

Unlike the learning layer 110, the inference layer 120 reacts over the course of a gait cycle. The inference layer 120 can quickly apply rules it has learned from the learning layer 110 to situations as they arise and respond accordingly. For example, the response time of the inference layer 120 can be on the order of tenths of seconds.

Contextually, the inference layer 120 can be thought of as an intermediate data abstraction level, where most of the work consists of extracting features from an input stream comprising pre-processed data. The data can be processed and characterized to achieve objectives including, but not limited to, managing the POD 100 such that system behavior matches the activity being undertaken by the user and quantifying system performance in terms of overall functionality of the POD.

The intermediate position the inference layer 120 occupies within the hierarchy can serve an additional purpose: protecting the reactive layer 130 from the learning layer 110. That is, the inference layer 120 can prevent the learning layer 110 from changing parameters directly used by the reactive layer 130, which may lead to system instability. Instead, the learning layer 110 can suggest that the inference layer 120 take a particular action or slightly alter a variable in a data set.

The reactive layer 130, in certain embodiments, represents the lowest abstraction level of the control structure. The reactive layer 130 can directly enforce the desired behavior that is responsive to the activities undertaken by the user. Here, the desired behavior can be determined by the inference layer's rule set, which the learning layer 110 can alter.

In other words, similar to the general behavior of the human arc-reflex, the reactive layer 130 of certain embodiments can immediately enforce a predefined behavior based on a reduced set of sensory input and estimates. The time frame for the operation of the reactive layer 130 can be on the order of milliseconds. More specifically, the reactive layer 130 can handle the motor control laws of the prosthetic system. For example, the reactive layer 130 implement one or more types of actively modified joint behavior or dynamically modify an amount of power supplied for (or a power level of) a particular type of actively modified joint behavior.

Although the control system architecture presented in FIG. 1 may appear to hierarchical in nature, the system can have a parallel in structure by allowing the reactive layer 130 to manage itself. For example, in certain embodiments, the reactive layer 130 can use a knee torque sensor output to implement a low-level impedance controller to manage the system's actuator behavior in real-time. Alternatively, the same knee torque sensor output can be used by the inference layer 120 to detect the occurrence of a transition in the user's gait activity to downwards walking. Both decisions present different levels of complexity can be made independently by the different control layers.

Additional details regarding control layers useable with certain embodiments of the invention are disclosed in U.S. Patent Publication No. 2011/0125290 (the "'290 publication"), published May 26, 2011, entitled "Reactive Layer Control System For Prosthetic And Orthotic Devices," and U.S. Pat. No. 8,915,968, issued Dec. 23, 2014, entitled "Prosthetic and Orthotic Devices and Methods and Systems for Controlling the Same," which describe various embodiments and features related to POD systems, each of which is hereby incorporated herein by reference in its entirety.

Configuring the inference layer control system based on these three rationales is motivated by the possibility that there may be no single control system formulation that can respond to all user needs associated with an actuated POD 100 in all situations.

Overview of the POD

Figure 2:
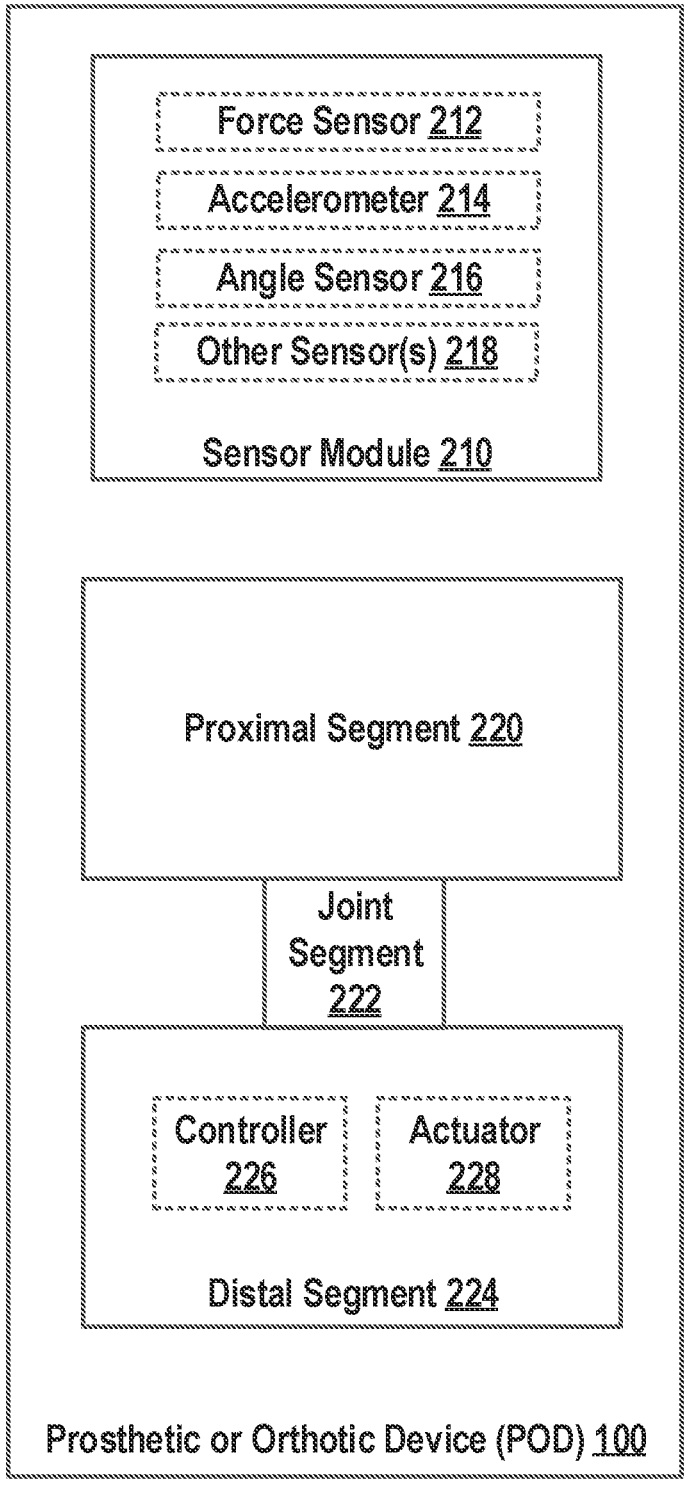
FIG. 2 illustrates a block diagram of a POD having an electronically controlled prosthetic joint.

FIG. 2 illustrates a block diagram of POD 100. In this example, the POD 100 includes a sensor module 210, a proximal segment 220, a joint segment 222, a distal segment 224, an actuator 228, and a controller 226.

The proximal segment 220 of the POD 100 can include a socket to hold the stump of an above-knee, below-knee or other amputee. The proximal segment 220 can be connected to the distal segment 224 via the joint segment 222. Although generally described herein as a prosthetic knee, the joint segment can be any of knee joint, an ankle joint, hip joint, elbow joint, or the like. In some cases, the POD 100 can include both a knee joint and an ankle joint. The controller 226, actuator 228, or sensor module 210 can be located in any number of locations, including the proximal segment 220, the distal segment 224, or the joint segment 222. The actuator 228 can be implemented using a linear or rotary actuator. Moreover, other types of actuators may be used without departing from the spirit and scope of the description.

The controller 226 or another processing device can determine one or more of various gait parameters associated with the POD 100. For example, as described herein, the controller 226 can determine one or more gait parameters based on data received from the sensor module 210. Any calculations or determinations described herein can be performed by any combination of the POD 100, the controller 226, or another processing device. Accordingly, although some of the embodiments described herein may describe one or more determinations or calculations being performed by the POD 100, it should be noted that, in some cases, each of the POD 100, the controller 226, or another computing device can perform all, none, or some of the calculations or determinations described herein.

The sensor module 210 of the POD 100 can capture information relating to load distribution, angles, orientation, braking, position, movement or other data of the POD 100. This information may be processed in real-time and communicated to the controller 226, a monitoring device (not shown), or the like. The sensor module 210 can include one or more sensors including, but not limited to, a force sensor 212, an acceleration or orientation sensor 214 (for example, an accelerometer, a gyroscope, an orientation sensor, or a gravity sensor), an angle sensor 216, or one or more other sensors 218.

The force sensor 212 can provide force measurement data corresponding to an amount of load applied to the POD 100 by a user. For example, the force sensor 212 can be configured to measure a component of force applied to the POD 100 from the ground or other supporting surface in a direction substantially along or parallel to a shin longitudinal axis. In some cases, the force sensor 212 can be implemented as a load cell.

Force measurement data from the force sensor 212 can be used to determine various gait parameters. For example, using the force measurement data, the controller 226 can determine whether the POD 100 is on or off the ground or other supporting surface. In some cases, force measurement data can be used to determine an estimated weight of the user. For example, provided that a user delivers largely symmetric loading across the POD 100 and the sound limb, the weight of the user can be approximately equal to double the force measurement. Similarly, if the weight of the user is known or has been determined, the force measurement data can be used to determine a load placed on the POD 100, a load placed on the sound limb, or a weight distribution between the two. For example, the force measurement data can be used to determine whether a user is symmetrically loading the POD 100 and sound limb, or whether one of the POD 100 or sound limb is loaded more heavily. That is, a force measurement corresponding to less than half of the user's body weight can indicate that the user is more heavily loading the sound limb, while a force measurement corresponding to more than half of the user's body weight can indicate that the user is more heavily loading the POD. Accordingly, the controller 226 can utilize the force measurement data from the force sensor 212 to determine how heavily the user is loading the POD 100 at any particular time or over any particular time period.

In some cases, the force sensor 212 can include multiple force sensors, from which information regarding how the user distributes load across the POD 100 can be determined. For example, using force measurement data from a front force sensor configured to measure load on the front or toe end of the POD 100 and from a back force sensor configured to measure load on the rear or heel end of the POD 100, the controller 226 can determine the user's front/back load distribution. That is, a higher toe end load (as compared to the heel end load) can indicate that the user is leaning forward on his toes, while a higher heel end load (as compared to the toe end load) can indicate that the user is leaning backward on his heels. Similar determinations can be made if the force sensor 212 includes a right force sensor configured to measure load on the right side of the POD 100 and a left force sensor configured to measure load on the left side of the POD 100. That is, a higher right side load (as compared to the left side load) can indicate that the user is leaning to the right, while a higher left side load (as compared to the right side load) can indicate that the POD 100 is leaning to the left. In some cases, the system 200 can include any combination of one or more of a left side force sensor, a right side force sensor, a heel force sensor, a toe force sensor, or various other force sensors configured to measure at various locations of the POD 100.

The acceleration or orientation sensor 214 can provide acceleration data corresponding to acceleration of the POD 100 in one or more axes. For example, the acceleration or orientation sensor 214 can be configured to measure acceleration of the POD in multiple axes, such as two or three substantially mutually perpendicular axes. The acceleration or orientation sensor 214 can be configured to measure an orientation of at least one of the proximal segment 220 or the distal segment 224. In some cases, the acceleration or orientation sensor 214 can be implemented as an accelerometer. The sensor module 210 may include one or more other types of sensors in combination with, or in place of, an accelerometer. For example, the sensor module 210 may include a gyroscope configured to measure the angular speed of body segments, an orientation sensor, or a gravity sensor.

The acceleration or orientation data from the acceleration or orientation sensor 214 can be used to determine one or more gait parameters. For example, using the acceleration or orientation data, the controller 226 can determine a shank angle, which can be described as an angle of the line of the shank (for example, corresponding to a shin of the user) relative to a line of the foot of the POD 100 or a walking surface. In some cases, the shank angle can be described in degrees. For example, the shank angle can be described in degrees of incline or recline from the vertical, measured in the sagittal plane. That is, an inclined shank angle can indicate that the POD 100 is leaning forward from the vertical, while a reclined shank angle can indicate that the POD is leaning backward from the vertical. Similarly, in some cases, the shank angle is described in degrees from the vertical. That is, a zero shank angle can indicate that the POD 100 is vertical; a positive shank angle can indicate that the POD 100 is leaning forward; and a negative shank angle can indicate that the POD 100 is leaning backward. Similar determinations can be made for directions other than forward and backward. For example, using the acceleration or orientation data, the controller 226 can determine to what degree (if at all) the POD 100 is leaning in any direction, such as left, right, front, back, etc. Accordingly, the controller 226 can utilize the acceleration or orientation data from the acceleration or orientation sensor 214 to determine whether the user is balanced or leaning during any of the various user-POD interactions, as described herein.

The angle sensor 216 can provide angle measurement data corresponding an angle between the proximal segment 220 and the distal segment 224. As a non-limiting example with respect to a prosthetic knee, proximal segment 220 can extend from the individual's thigh and the distal segment can correspond to the user's shank (for example, corresponding to a user's shin), and the angle sensor 216 can be configured to detect or measure a knee rotation angle (sometimes referred to as the knee angle or the joint angle). Accordingly, using angle measurement data from the angle sensor 216, the controller 226 can determine the joint angle, and thus a degree to which the joint segment 222 is flexed or extended. For example, a 180 degree knee rotation angle can indicate that the POD 100 is straight (for example, the user's thigh and shank are parallel), while a 90 degree knee rotation angle can indicate that the POD is bent such that the user's shank is angled at 90 degrees relative to the user's thigh. Accordingly, the angle measurement data from the angle sensor 216 can be used determine whether the POD 100 is angled, and, in some cases, the degree to which the POD 100 is angled.

As another non-limiting example with respect to a prosthetic angle, the proximal segment 220 can extend from the user's shank and the distal segment 224 can correspond to the user's foot, and the angle sensor 216 can be configured to detect or measure an ankle rotation angle. Similarly, determinations can be made for a prosthetic hip, elbow, or the like.

Other suitable angle sensing devices may be utilized to determine the angle data. For example, in some cases, the angle sensor includes a potentiometer. Power can be supplied to one end of the potentiometer while the other end is held at ground. In some cases, this can provide a signal output proportional to a position between 0° (for example, the POD 100 is completely bent) and 180° (for example, the POD 100 is straight). Other suitable angle sensing devices can include optical or magnetic shaft encoders or the like.

In some cases, the actuator 228 can be configured to provide resistive forces (sometimes referred to as resistive braking) to substantially simulate the position or motion of a natural knee joint during ambulation or other locomotory or stationary activities performed by a user. In other words, the actuator can act as a brake, varying its resistance to motion. In some cases, the controller 226 can determine various braking indicators related to the braking effect of the POD 100, including, but not limited to, resistance, torque torsional resistance generated, or the level of damping. Other suitable sensing devices may be utilized to determine one or more parameters related to the braking effect of the POD 100 and/or torque at the joint of the POD 110. For example, one or more sensing devices can be used to determine or compute a component of torque applied to an actuator 228, which can, for example, adjust a braking torque applied by the actuator 228 to the POD 100. In some cases, the controller 226 can similarly compute the component of torque applied to the actuator 228 using the force measurement data from the force sensor 212.

Example POD

Figure 3A:
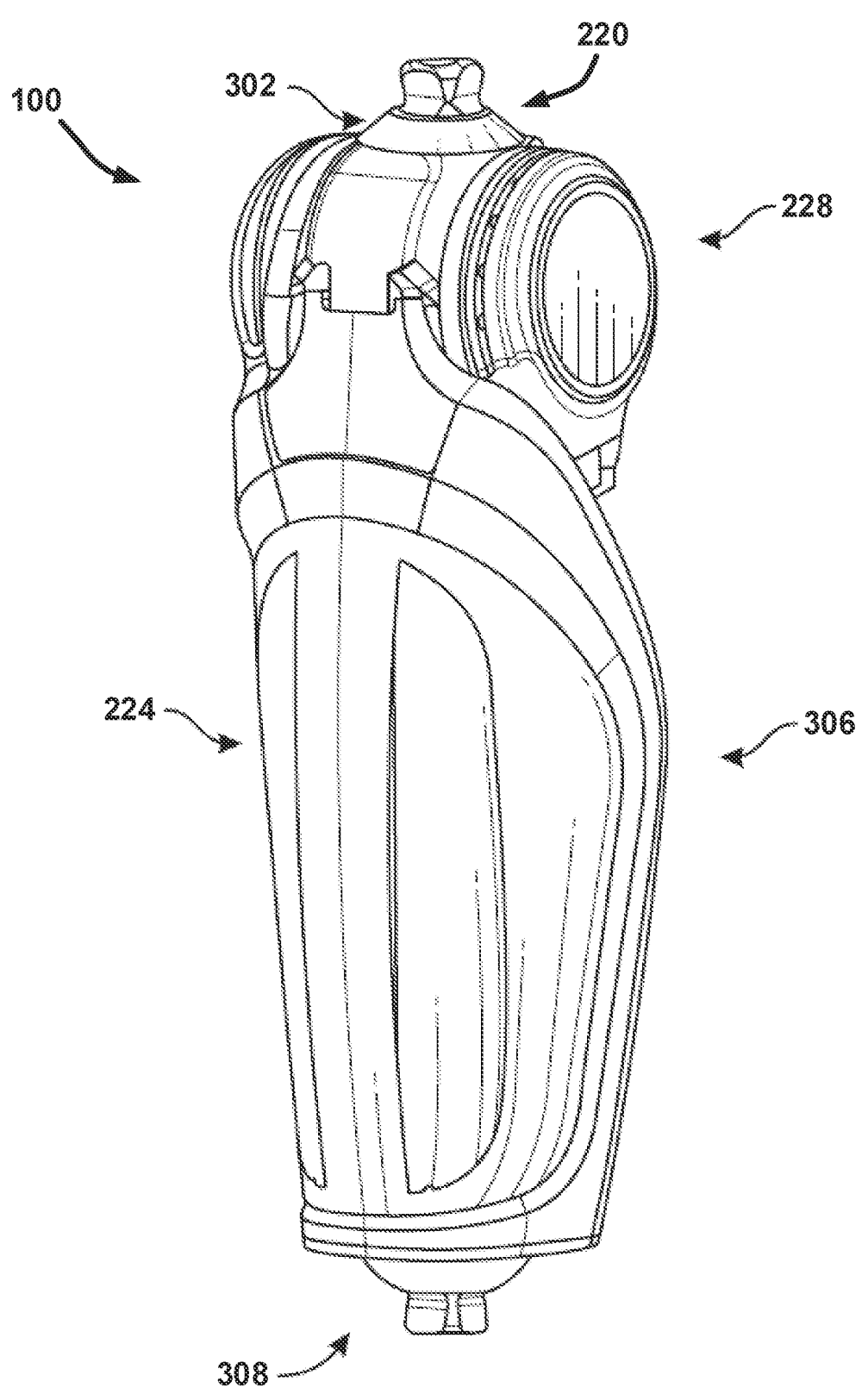
FIGS. 3A and 3B illustrate example POD.
Figure 3B:
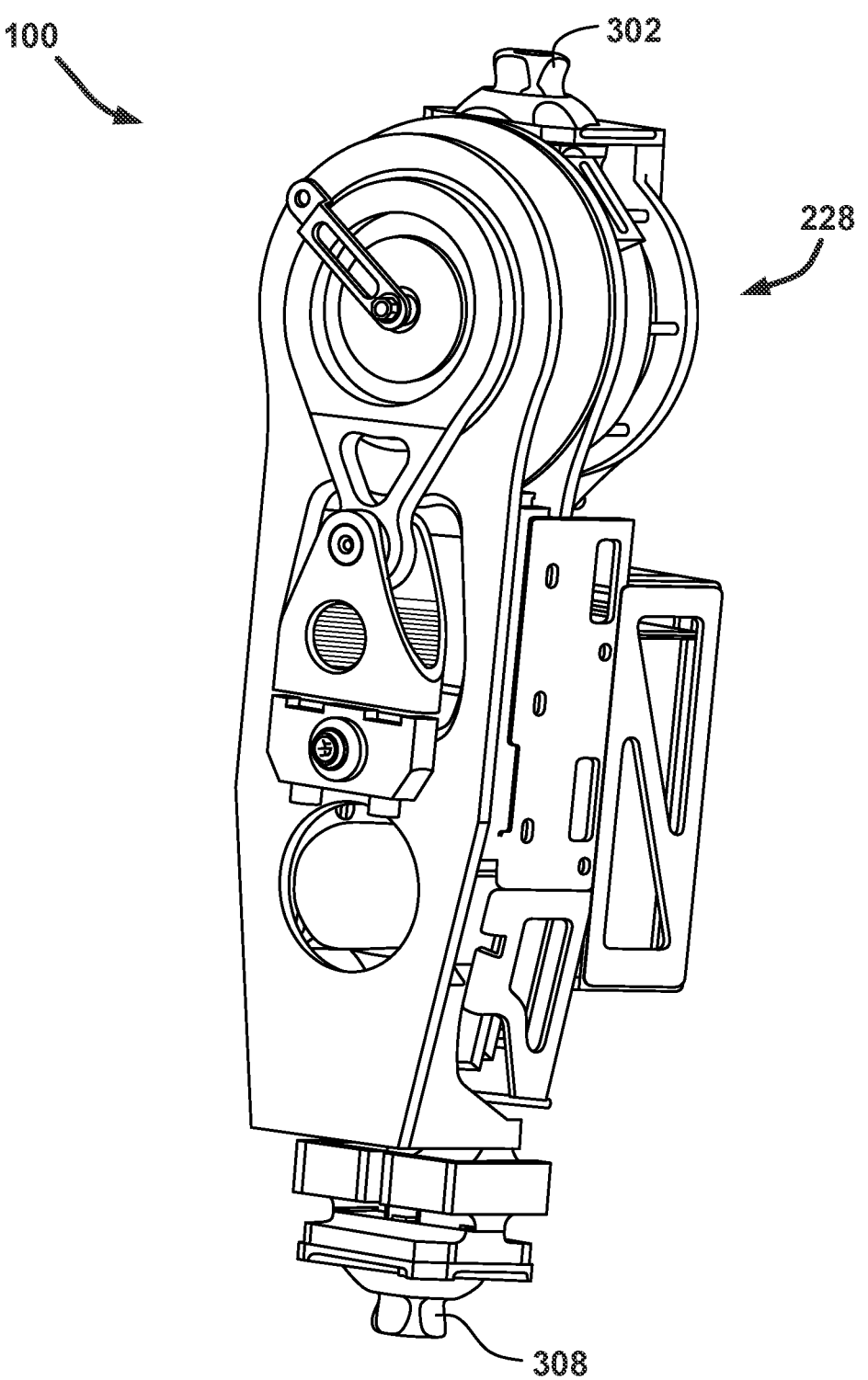

FIGS. 3A and 3B illustrate examples of a POD 100. The PODs 100 illustrated in FIGS. 3A and 3B implement a knee joint and may be connected to a user's residual limb, such as a thigh or a stump of an above-knee amputee, through a socket (not shown) via the proximal connector 302 on its proximal segment 220. The proximal connector 302 may be pyramidal in shape. In the examples of FIGS. 3A and 3B, the POD 100 is a lower-limb prosthetic device, shown as a shank. The proximal connector 302 may be coupled to an actuator 228, which can rotate with respect to a body 306. The actuator 228 may be motorized. Rotation of the actuator 228 may cause rotation of the proximal connector 302 with respect to the body 306, and vice versa. In some aspects, the body 306 may be on or form a shank portion of the POD 100. The body 306 may include electronic components, sensors, etc. (not shown) required for the POD 100 to operate, although in some aspects these components may be located elsewhere, such as on a peripheral device or within remote components. In some cases, the POD 100 may be connected to a prosthetic or orthotic ankle or foot (not shown) via the distal connector 308 located on a distal segment 224 of the POD 100. The POD 100 may be connected with or include a prosthetic hip, prosthetic thigh, prosthetic foot, prosthetic ankle, or the like.

Example PODs are described in U.S. Pub. No. 2009/0299480, filed Jul. 7, 2009, entitled "Joint Actuation Mechanism for a Prosthetic or Orthotic Device Having a Compliant Transmission," U.S. Pub. No. 2011/0125290, filed May 26, 2011, entitled "Reactive Layer Control System For Prosthetic And Orthotic Devices," each of which describes various embodiments and features related to POD systems and each of which is hereby incorporated herein by reference in its entirety.

Impedance Controller

Figure 4:
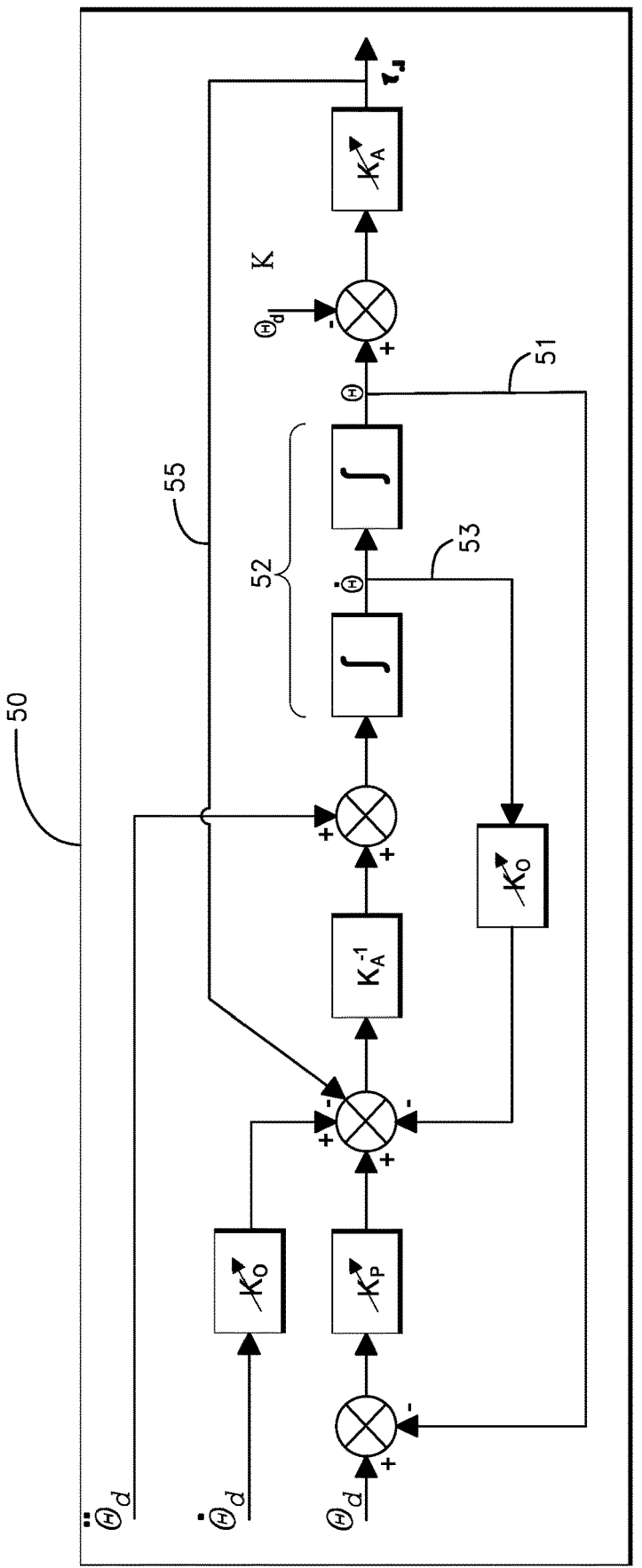
FIG. 4 illustrates a block diagram of an example control loop of a controller of the POD.

FIG. 4 illustrates a block diagram of an example control loop 400 of the controller 226 of the POD 100. The control loop 400 can be implemented at the reactive layer 130. In some cases, the control loop 400 allows the controller 226 to manage the actuator 228 or support the implementation of various behaviors by the actuator 228.

In some cases, based on the control loop 400, the controller 226 can enter a passive mode. For example, based on the inference layer determining that the user of the POD 100 is standing and/or based on a determination that one or more gait parameters do not satisfy one or more gait parameter thresholds, the inference layer can communicate a command to a reactive layer to enter a passive mode. During the passive mode, the actuator can exhibit a FR behavior during some of or the entire stance phase and a FF behavior during some of or the entire swing phase.

In some cases, based on the control loop 400 the controller 226 can enter an active mode. For example, based on the inference layer determining that the user of the POD 100 is walking and/or a determination that one or more gait parameters satisfy one or more gait parameter thresholds, the inference layer can communicate a command to a reactive layer to enter an active mode.

In the active mode, the controller can cause the actuator to exhibit a FR behavior during the stance phase and a FF behavior during swing phase. For example, in the active mode, the controller can cause the actuator to exhibit the FR behavior between foot strike and midstance. As another example, in the active mode, the controller can cause the actuator to exhibit the FF behavior for at least some duration of time between toe-off and a first heel rise target, and between a second heel rise target and a first knee extension target. The first heel rise target can occur during the initial swing subphase. For example, the first heel rise target can occur between toe-off and maximum knee flexion. The first knee extension target can occur after the maximum knee flexion during swing phase.

Furthermore, in the active mode, the controller (e.g., reactive layer) can cause the actuator to exhibit one or more of types of actively modified joint behavior, such as toe-off assist behavior, a braking behavior, or a bumper avoidance behavior. As described herein, the toe-off assist behavior can correspond to an active flexion of the joint (e.g., knee) at the end of the stance phase by the actuator of the POD, braking behavior can correspond to the actuator applying a torque to the joint to decelerate flexion of the joint, and the bumper avoidance behavior can correspond to the actuator applying a torque to the joint to decelerate extension of the joint.

In certain cases, in active mode, the controller (e.g., reactive layer) causes the actuator to exhibit toe-off assist behavior during stance phase after exhibiting FR behavior. In some cases, the reactive layer causes the actuator to exhibit the braking behavior and bumper avoidance behavior during swing phase. In certain cases, the braking behavior follows a first FF behavior and the bumper avoidance behavior follows a second FF behavior.

In some cases, the actuator can exhibit the braking behavior based on different gait events or thresholds during gait. For example, the actuator can exhibit the braking behavior based for at least some duration of time between the first heel rise target and the second heel rise target. The second heel rise target can occur during the initial swing subphase. For example, the second heel rise target can correspond to maximum knee flexion (e.g., about 60° flexion) during swing phase.

In certain cases, the actuator can exhibit the bumper avoidance behavior based on different gait events or thresholds during gait. For example, the controller can cause the actuator to exhibit the bumper avoidance behavior for at least some duration of time between the first knee extension target and a second knee extension target. The second knee extension target can occur during the terminal swing subphase. For example, the second knee extension target can correspond to maximum knee extension during swing phase.

In some cases, the different types of actively modified joint behavior can be activated concurrently as part of the active mode. For example, the toe-off assist behavior, braking behavior, and the bumper avoidance behavior can be activated when the controller enters the active mode. In such a scenario, the toe-off assist behavior can be included as part of the stance phase and the braking behavior and the bumper avoidance behavior can be included as part of the swing phase.

In some cases, the active mode, passive mode, FR behavior, FF behavior, braking behavior, or bumper avoidance behavior can be implemented through appropriate selection of gain values. Example gain values and control loops of the controller 226 are described in '290 publication.

In certain cases, different types of actively modified joint behavior can be activated at different times or based on different thresholds, or some actively modified joint behaviors may be activated together and/or based on the same gait parameter thresholds while other actively modified joint behaviors may be activated at different times and/or based on different gait parameter thresholds. In some cases, in active mode, the controller determines whether to activate one or more of types of actively modified joint behavior based on the value of one or more gait parameters. For example, based on a first gait parameter satisfying a first gait parameter threshold, the controller can activate the braking behavior for inclusion as part of the swing phase. As another example, based on a second gait parameter (or the first gait parameter) satisfying a second gait parameter threshold, the controller can activate the bumper avoidance behavior for inclusion as part of the swing phase. As yet another example, example, based on a third gait parameter (or the first or second gait parameter) satisfying a third gait parameter threshold, the controller can activate the toe-off assist behavior. Accordingly, in some cases, one type of actively modified joint behavior may be activated while another is not. For example, the braking behavior and bumper avoidance behavior can be activated at 80 steps/minute and the toe-off assist behavior can be activated at 100 steps/minute.

As described herein, in some cases, the actively modified joint behaviors can be activated at different power levels and then ramp up depending on the gait parameter and/or demands of the activity. For example, the toe-off assist behavior (and/or the braking behavior and/or the bumper avoidance behavior) can be activated at 25% at 80 steps/minute and linearly increase up to 100% at 110 steps/minute or increase in 25% increments for each +10 steps/minute increase.

Figure 5:
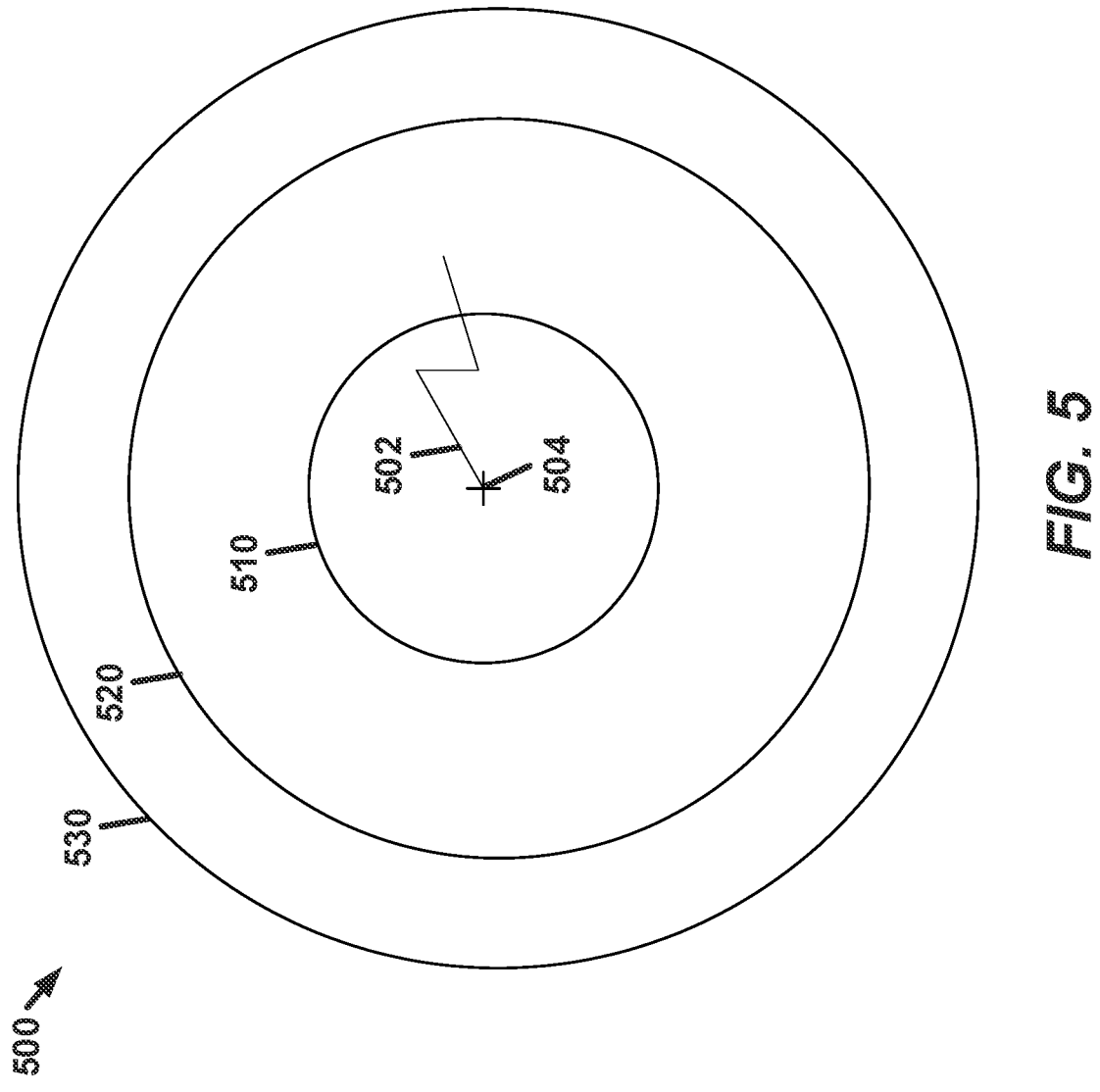
FIG. 5 depicts an operational map having a set of concentric circles which represent a control system operation space along a gait parameter.

FIG. 5 depicts an operational map 500 for a hybrid control scheme having a set of concentric circles 510, 520, 530, which represent control system operation spaces (or subspaces) along a gait parameter. In the illustrated example, each of the concentric circles 510, 520, 530 represents a different gait parameter threshold. Progression of the gait parameter value in the operational space is represented by the line 502, which originates at the origin 504. As the user progresses in the operational environment (and the gait parameter value changes), the line 502 eventually satisfies the first gait parameter threshold 510. As a non-limiting example, consider a scenario in which the inner circle 510 represents standing and the area outside the outer circle 530 represents walking. In such a scenario, the control system operation includes two intermediate behavior zones (or sub-spaces) between standing and walking (between circles 510 and 520 and between circles 520 and 530).

In some cases, satisfying the first gait parameter threshold 510 can cause the POD 100 to modify its behavior to better adjust to the reality of the environment as perceived by the user. For example, in some cases, satisfying the first gait parameter threshold 510 causes the POD 100 to transition from passive mode to active mode (and/or to activate one or more actively modified joint behavior). As yet another example, in some cases, satisfying the first gait parameter threshold 510 causes the POD 100 to remain in the same mode (e.g., remain in active mode), but modify at least one of the type of actively modified joint behavior or power level of actively modified joint behavior that is provides to the user. For example, satisfying the first gait parameter threshold 510 can cause the POD 100 to activate at least one of toe-off assist behavior, the braking behavior, or the bumper avoidance behavior, which may have been inactive when the first gait parameter threshold 510 was not satisfied. As another example, satisfying the first gait parameter threshold 510 can cause the POD 100 to modify the actively modified joint behavior of toe-off assist behavior, for example by increasing the flexion caused by the actuator.

Similarly, satisfying the second gait parameter threshold 520 can cause the POD 100 to activate one or more additional actively modified joint behaviors, and/or increase a power level of one or more actively modified joint behaviors. For example in the second sub-space (between circle 510 and circle 520), toe-off assist may not be activated or may be operating at a power level of 50%. In such a scenario upon transitioning to the third sub-space (between circle 520 and circle 530), the toe-off assist may be activated or its power level may be changed to 75%.

In like manner, satisfying the third gait parameter threshold 530 can cause the POD 100 to activate one or more additional actively modified joint behaviors and/or increase a power level of one or more actively modified joint behaviors. With continued reference to the scenario above, upon transitioning to the fourth sub-space (outside circle 530), if the toe-off assist was not previously activated it can be or if it was operating at 75% it can be changed to operate at 100%. In addition, as mentioned, in the fourth sub-space, the POD can transition from a standing activity state to a walking activity state, which can introduce additional controller gains and/or changes.

Although described as adding actively modified joint behaviors, increasing the power levels of actively modified joint behaviors, transitioning from passive to active, and transitioning from standing to walking, it will be understood that the hybrid control scheme can also be used to transition in any direction between activities or modes, to decrease power levels of actively modified joint behaviors, or deactivate actively modified joint behaviors. For example, if the gait parameter moves from the fourth sub-space to the third, second, or first sub-space (within circle 510), the controller can deactivate actively modified joint behaviors, reduce power levels of actively modified joint behaviors, transition from active mode to passive mode, and/or transition from a walking activity to a standing activity, etc.

As another example, if the POD is in an active mode or walking state in the first sub-space with one or more actively modified joint behaviors at particular power levels, then moving to the second, third, or fourth sub-spaces, can cause the POD to reduce power levels of actively modified joint behaviors, deactivate actively modified joint behaviors, transition from an active mode to a passive mode, and/or transition from walking to standing.

In any case, the sub-spaces of the hybrid control scheme, the passive/active modes, the different actively modified joint behaviors within the active mode, and/or the different power levels of actively modified joint behaviors within the active mode can provide flexible and dynamic phases between discrete controller states, thereby smoothing the transition between discreet activities (e.g., standing and walking) in a physiologically compliant way. In this manner, the hybrid control mode can improve the usability and functionality of a POD for a user.

The operational map can have multiple operational points or multiple operational parameters, which would be represented by a separate map in this case. The hybrid control system associates various or specific behavior associated with each region created by the space between the boundary lines.

Different gait parameters can be used as desired. For example, the gait parameter can include any one or more of user forward speed, walking cadence, stance time, thigh angle excursion amplitude during stance phase, absolute thigh angle at toe-off, absolute thigh angle at foot strike, knee torque amplitude at late stance, number of steps completed while achieving a minimum swing flexion amplitude, thigh or shank sagittal plane rotational or linear acceleration, thigh or shank sagittal plane rotational speed amplitude, ground reaction force amplitude at foot strike, ground reaction force amplitude on toe in late stance, user center of mass linear acceleration, a ground interaction, an amount of load placed on the POD, a shank angle, or a joint angle. Any one or any combination of gait parameters and corresponding gait parameter thresholds can be used.

For example, the origin 504 can represent null velocity, and each of the concentric circles 510, 520, 530 can correspond to various velocity thresholds (for example, 0.8 m/sec, 1.2 m/sec, etc.). In some such cases, based on the user forward speed satisfying the first velocity threshold (e.g., 0.8 m/s), the controller can select active mode, cause the actuator to activate at least one of toe-off assist behavior, the braking behavior, or the bumper avoidance behavior, or modify the power level of an actively modified joint behavior (for example, change toe-off assist behavior from 50% power to 75% power).

As another example, the gait parameter can be walking cadence and the first gait parameter threshold can be a cadence threshold. In some such cases, based on the walking cadence satisfying the cadence threshold (e.g., 80 steps per min), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be stance time and the first gait parameter threshold can be a stance time threshold. In some such cases, based on the stance time satisfying the stance time threshold (e.g., 400 ms), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be thigh angle excursion amplitude during stance phase and the first gait parameter threshold can be an angle threshold. In some such cases, based on the thigh angle excursion amplitude during stance phase satisfying the angle threshold (e.g., 30 degrees), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be absolute thigh angle at toe-off and the first gait parameter threshold can be an angle threshold. In some such cases, based on the absolute thigh angle at toe-off satisfying the angle threshold (e.g., 10 degrees), the controller can select active mode, cause the actuator to activate at least one of toe-off assist behavior, the braking behavior, or the bumper avoidance behavior, or modify the capacity of an actively modified joint behavior (for example, change bumper avoidance from 50% power to 75% power).

As another example, the gait parameter can be absolute thigh angle at foot strike and the first gait parameter threshold can be an angle threshold. In some such cases, based on the absolute thigh angle at foot strike satisfying the angle threshold (e.g., 15 degrees), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be knee torque amplitude at late stance and the first gait parameter threshold can be a torque threshold. In some such cases, based on the knee torque amplitude at late stance satisfying the torque threshold (e.g., 10 N·m), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be the number of steps completed while achieving a minimum swing flexion amplitude and the first gait parameter threshold can be a step threshold. In some such cases, based on the number of steps completed while achieving a minimum swing flexion amplitude satisfying the step threshold (e.g., 2 steps), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be thigh or shank sagittal plane rotational or linear acceleration and the first gait parameter threshold can be an acceleration threshold. In some such cases, based on the thigh or shank sagittal plane rotational or linear acceleration satisfying the acceleration threshold (e.g., 0.8 m/s), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be thigh or shank sagittal plane rotational speed amplitude and the first gait parameter threshold can be a speed threshold. In some such cases, based on the thigh or shank sagittal plane rotational speed amplitude satisfying the speed threshold (e.g., 300 degrees per second), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be ground reaction force amplitude at foot strike and the first gait parameter threshold can be a weight threshold. In some such cases, based on the ground reaction force amplitude at foot strike satisfying the weight threshold (e.g., 95% of the user's body weight), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

As another example, the gait parameter can be ground reaction force amplitude on toe in late stance and the first gait parameter threshold can be a weight threshold. In some such cases, based on the ground reaction force amplitude on toe in late stance satisfying the weight threshold (e.g., 90% of the user's body weight), the controller can select active mode, cause the actuator to activate at least one of toe-off assist behavior, the braking behavior, or the bumper avoidance behavior, or modify the capacity of an actively modified joint behavior (for example, change toe-off assist behavior from 50% power to 75% power).

In some cases, the controller (reactive layer) can use gait events to change between the different behaviors within a gait cycle. In certain cases, the gait events can be used to determine when to exhibit the FR behavior, FF behavior, braking behavior, or bumper avoidance behavior. For example, in the active mode, based on a determination that a foot associated with the POD has left ground the actuator can exhibit the force following behavior. As another example, in the active mode, based on a determination that a first heel rise target has been reached, the actuator can begin the braking behavior to decelerate flexion of the powered prosthetic knee until the heel reaches a second heel rise target. As another example, in the active mode, based on a determination that the second heel rise target has been reached, the actuator can exhibit the force following behavior until a first knee extension target is reached. As another example, in the active mode, based on a determination that the knee associated with the powered prosthetic knee has reached the first knee extension target, the actuator can act as a damper relative to a velocity of the first limb member to exhibit the bumper avoidance behavior.

Figure 6:
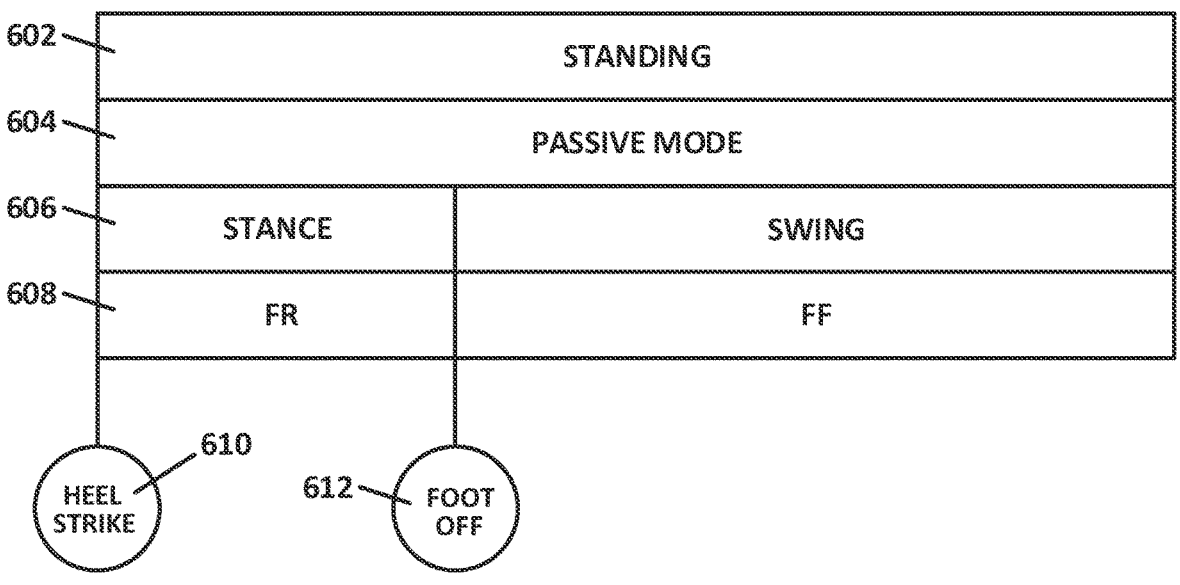
FIG. 6 is a sequence diagram illustrating phases, actuator behaviors, and gait events for management of a standing activity.

FIG. 6 is a sequence diagram 600 illustrating phases, actuator behaviors, and gait events for management of a standing activity. In some cases, the controller 226 (for example, using the inference layer 120) of a POD 100 determines the current activity being undertaken by the user is standing. For example, in the illustrated example of FIG. 6, the top entry 602 represents the output of the inference layer execution, which in this case is "Standing." In some cases, based on the current activity being undertaken, the controller 226 (for example, using the reactive layer 130) can select a controller mode (for example, active mode or passive mode). For example, in the illustrated example, based on a determination that the current activity being undertaken by the user is standing, the actuator 228 can operate in passive mode. The entry 604 represents the output of the inference layer execution, which in this case is "Passive Mode." In some cases, the controller 226 may not determine an activity being undertaken by the user. For example, the controller 226 may select a controller mode based one or more gait parameters without regard to a determined activity being of the user.

As illustrated in FIG. 6, in passive mode, the controller can cause the actuator to exhibit a FR behavior during some of or the entire stance phase and a FF behavior during some of or the entire swing phase. Furthermore, in some cases, the controller 226 (for example, using the reactive layer 130) can determine the phase based on the occurrence of the gait events. For example, based on gait event 610 (foot strike), the controller 226 can determine that the POD 100 is currently operating in, or initiating, stance phase. As another example, based on gait event 612 (toe-off), the controller 226 (for example, using the reactive layer 130) can determine that the POD 100 is currently operating in, or initiating, swing phase. Furthermore, in some cases, the controller 226 associates the phase with specific actuator behaviors, such as FR behavior or FF behavior. In the example of FIG. 6, stance phase is associated with the FR behavior and swing phase is associated with the FF behavior.

Figure 7:
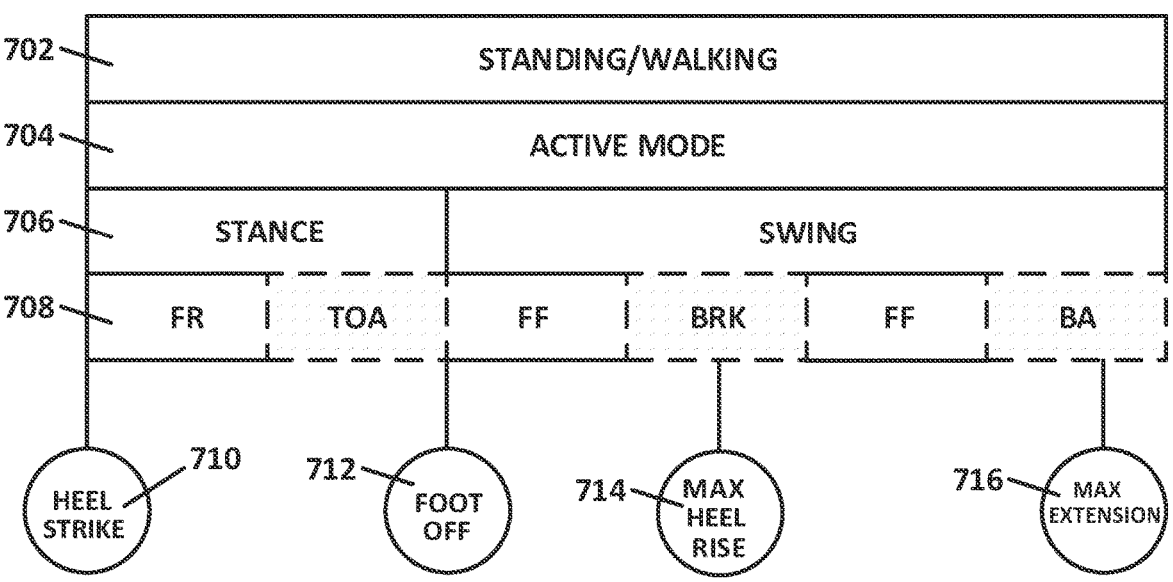
FIG. 7 is a sequence diagram illustrating phases, actuator behaviors, and gait events for management of a standing/walking activity.

FIG. 7 is a sequence diagram 700 illustrating phases, actuator behaviors, and gait events for management of a standing/walking activity. In some cases, the controller 226 (for example, using the inference layer 120) of a POD 100 determines the current activity being undertaken by the user is standing/walking. In the illustrated example of FIG. 7, the top entry 702 represents the output of the inference layer execution, which in this case is "Standing/Walking." In some cases, based on the current activity of the user, the controller 226 can select the controller mode, which in this case is active mode 704. In the illustrated embodiment of FIG. 7, the controller 226 can select active mode based on a determination that the current activity being undertaken by the user is walking. However, in some cases, the controller 226 may not determine an activity of the user and/or may select the controller mode independent of the activity of the user. For example, the controller 226 may select a controller mode based one or more gait parameters without regard to the activity of the user.

In some cases, the controller 226 can detect gait phases of the user based on gait parameter data. For example, based on a determination that a heel or foot of the POD contacts the walking surface (generally referred to as foot strike 710 or foot strike) the controller 226 can determine that stance phase has started and/or swing phase has ended. Furthermore, based on a determination that a toe of the POD rises from the walking surface (generally referred to as toe off 712) the controller 226 can determine that stance phase has ended and/or swing phase has started.

Each gait cycle or stride can have two phases: stance phase, the phase during which the foot remains in contact with the ground; and swing phase, the phase during which the foot is not in contact with the ground. Depending on the controller mode, the controller 226 may associate the gait phases or portions thereof with specific actuator behaviors. For example, in passive mode, the controller 226 can associate the FR behavior with stance phase and the FF behavior with swing phase. Furthermore, in active mode, the controller 226 can associate at least one of the FR behavior or toe-off assist behavior with stance phase and at least one of the FF behavior, the braking behavior, or the bumper avoidance behavior with swing phase.

In some cases, each of the phases is associated with a single behavior. For example, as illustrated in FIG. 6, stance phase can be associated with the FR behavior and swing phase can be associated with FF behavior. In some cases, the phases can be further defined into two or more sub-phases or be associated with two or more behaviors. For example, as illustrated in FIG. 7, stance phase can be associated with a FR sub-phase and a toe-off assist behavior. In this case, the FR sub-phase makes use of the impedance controller to actively lock the POD 100 using the torque feedback to define the actuator effort, leading to a locked knee independent of the amount of weight placed on it by the user or independent of the knee flexion angle. In some cases, based on gait event 712 (foot strike), the controller 226 (for example, using the reactive layer 130) can determine that the POD 100 is to transition to the FR behavior.

Toe-off assist behavior or pre-swing management typically extends from midstance until toe-off. In some cases, toe-off assist behavior makes use of the actuator 228 to actively flex the knee while the foot is still in contact with the ground. In some cases, proactive knee flexion before toe-off is detected allows to better align with the residual limb dynamics and ensure that the lower-limb transition into swing phase without the user feeling constrained in the forward progression motion or hip flexion motion. In some cases, the controller 226 (for example, reactive layer 130) can transition to toe-off assist behavior based on a reduction in the torque on the joint. For example, the controller 226 can determine a max torque on the joint during stance phase and as the torque is reduced from the max torque, the controller 226 can enter the toe-off assist behavior in preparation for toe-off or swing phase.

Continuing with the example of FIG. 7, following the gait event 714 (for example, toe-off), the POD is transitioned to a FF behavior, which allows the knee to coast under the general momentum imparted to the lower-limb by the toe-off assist behavior action and from the active hip flexion. Allowing the knee to coast without hard trajectory to follow can increase the system flexibility to user-based variations in gait style, as the knee will take direct input from the user body motion during that sub-phase of the gait cycle.

Once the knee flexion closes on the system-defined maximum heel rise target, reactive layer will change the behavior to Brake (BRK). Brake configures the impedance controller as a damper (velocity controller) and smoothly (e.g., systematically) decelerate the knee until maximum heel rise is reached, before accelerating (e.g., systematically) the knee back to support extension required to configure the lower-limb in preparation of the upcoming foot strike.

Once the knee extension speed reaches its minimum targeted value, the controller 226 (for example, the reactive layer 130) places the knee under the FF behavior to support the extension motion in an unconstrained manner and allow for optimal synergy between hip deceleration and knee dynamic support.

Once the knee reaches the terminal swing configuration, the controller 226 (for example, the reactive layer 130) modifies the actuator behavior to the Bumper Avoidance (BA). Under the Bumper Avoidance behavior, the controller 226 is configured as a position and velocity controller to smoothly decelerate the momentum of the extending knee and position the knee to the desired flexion angle in preparation of the upcoming foot strike.

Active Mode and Passive Mode

Some techniques for controlling an actuator 228 of an active POD 100 can utilize a hybrid control scheme, in which the actuator 228 can be controlled to dynamically vary between an active mode and a passive mode and/or dynamically vary the actively modified joint behavior provided during the active mode. For example, based on a determination that a gait parameter does not satisfy a gait parameter threshold or falls within a particular range, the POD can operate in passive mode, and based on a determination that the gait parameter satisfies the gait parameter threshold or falls within a second range, the POD can operate in active mode. In some cases, based on a gait parameter satisfying a gait parameter threshold, the POD can activate or deactivate one or more actively modified joint behavior features, such as one or more of the toe-off assist behavior, the braking behavior, and/or the bumper avoidance behavior. In certain cases, based on different gait parameter thresholds, different actively modified joint behavior features can be activated. In some such cases, based on a determination that the gait parameter satisfies a first gait parameter threshold (or a combination of gait parameters satisfy respective gait parameter thresholds) a first set of one or more actively modified joint behavior features can be activated/deactivated and based on a determination that the gait parameter satisfies a second gait parameter threshold (or a combination of gait parameters satisfy respective second gait parameter thresholds) a second set of one or more actively modified joint behavior features can be activated/deactivated. For example, based on a determination that a user has taken two steps at a cadence of at least 80 steps per minute, the POD can activate braking behavior and/or the bumper avoidance behavior, and based on a determination that the user has taken two steps at a cadence of at least 95 steps per minute, the POD can activate the toe-off assist behavior (in addition to the braking behavior and/or the bumper avoidance behavior).

In some cases, based on a gait parameter satisfying a gait parameter threshold, the POD can increase or decrease a level of one or more actively modified joint behavior features (e.g., changing the power level of toe-off assist behavior from 60% to 80%). In some cases, the controller continues to monitor one or more gait parameters and can dynamically switch between passive mode and active mode, or dynamically adjust the actively modified joint behavior features, based on the gait parameters.

Any combination of the aforementioned cases can be combined as desired. For example, based on one or more gait parameters satisfying respective gait parameter thresholds, the POD can change from a passive mode or active mode (or vice versa). Within the active mode, the POD can activate one or more actively modified joint behavior features concurrently or at different times. Further once a particular actively modified joint behavior feature is activated, it may operate at different levels of capacity. For example, at a cadence of 80 steps per minute, the POD may enter the active mode and activate toe-off assist behavior, braking behavior and/or the bumper avoidance behavior at 20%, 50%, or 100% of capacity. In cases where the actively modified joint behavior features are not activated to 100% of capacity, the percentages can increase based on different gait parameter thresholds and/or in proportion to the increase of the gait parameter. With continued reference to the example above, as the cadence increases, the percentages can increase until 100% is reached (e.g., at 110 steps per minute). In certain cases, the percentages can increase linearly with the increased cadence (or other gait parameter being used). In some cases, the percentages can increase in a step wise fashion (e.g., increase from 25% to 50% at 90 steps per minute, from 50% to 75% at 100 steps per minute and from 75% to 100% at 110 steps per minute).

Due to the loss of proprioception and control in the residual limb following amputation, optimal POD performance requirements can vary significantly when transitioning between tasks such as standing and walking. For example, when standing or operating the POD 100 in a confined space (for example, side stepping, taking small steps, etc.), it can be desirable for the POD 100 to provide stable stance support and allow for consistent transition from stance phase to swing phase. Furthermore, in some cases, when standing or operating the POD 100 in a confined space, there can be a limited need for actively managing the transition from the stance phase to swing phase (for example, providing an "actively modified joint behavior" to the user). For example, the user may not be ambulating with sufficient dynamics to require the knee to proactively initiate pre-swing phase and achieve correct synchronism with the residual limb and hip walking dynamics. For example, it may not be desirable to actively flex the knee, such as what occurs during toe-off assist behavior.

On the other hand, during walking or when the ambulation is transitioning from standing or confined ambulation towards cyclical walking, it can be desirable for the POD 100 to provide active support (for example, an actively modified joint behavior like toe-off assist behavior) of the swing phase or advanced management of the stance phase to swing phase transition. For example, in some cases, advanced management of the pre-swing phase of the gait cycle positively contributes to the energetics of walking and ensures synergy between the hip joint the residual limb and the prosthetic device operation. Thus, in some cases, use of a hybrid control scheme, where the behavior of the POD is dynamically modified during operation, can support the user more efficiently throughout a wider range of activities of daily living.

Additionally, using a hybrid control scheme can lessen or minimize negative effects associated with each type of system behavior or increase or maximize the positive effects of each type of system behavior. For example, passive PODs can provide good consistency and operational robustness. However, the stability and consistency provided in standing or confined ambulation often becomes a negative aspect of the passive POD when ambulation patterns become more dynamic, as the POD user then needs to adopt a pathological gait to accommodate the limited dynamics allowed by the passive POD. Otherwise, the user of the passive POD may end up limited in what he can achieve as far as functional performance. Furthermore, although active PODs can provide an actively modified joint behavior to the user, which can reduce energy consumption when ambulation patterns become more dynamic, in some cases, active PODs can be too proactive in providing actively modified joint behavior. For example, in activities or gait phases where little functional benefits arise from additional power injection or where control and consistency are desired, an active POD may perform worse than a passive POD.

Accordingly, in some cases, an actuator 228 can be controlled to perform like a passive POD. In other words, operation of the active POD can be adjusted so that the active POD replicates or is similar to the operation of the passive POD. In some cases, the controller can select passive mode while the POD is operating in a first operational sub-space, for example when the inference layer determines that the user is "standing," "shuffling," or not "walking" or determines that a gait parameter threshold is satisfied or is not satisfied.

In some cases, the controller causes the actuator to exhibit a toe-off assist behavior, in which an actuator actively flexes the knee while the foot is still in contact with the ground. If utilized, toe-off assist behavior (or pre-swing management) typically extends from midstance until toe-off. In some cases, in passive mode, the behavior of the actuator is modified so as to not exhibit a toe-off assist behavior during stance phase or to replace a toe-off assist behavior with FR (for example, which in effect can result in a FR sub-phase during most or all of stance phase). Furthermore, from midstance until toe-off, the actuator 228 can be left compliant and free to flex under the loading imposed by the user and its interaction with the environment. Since the POD is still under contact with the ground during that sub-phase, removal of the powered flexion (for example, toe-off assist behavior) or replacing it with a FR sub-phase can provide more control to the user to initiate the pre-swing cycle under his own control, which can aid in achieving desired timing in all steps. Additionally, such passive-mode behavior also allows the user to display higher variability in gait style and remove a need for the user to complete the toe-off assist behavior cycle following initiation.

In some embodiments, rather than replacing or removing toe-off assist behavior, the parameters of toe-off assist behavior can be changed in passive mode. For example, the amount of power used to actively move the joint during toe-off assist behavior can be reduced, thereby making it easier for a user to overcome the movement of the joint due to toe-off assist behavior. In some such cases rather than actively moving the knee during toe-off assist behavior using 100% power, the controller 226 can use 25% or 50% of power. As such the amount of force exerted by the user to overcome toe-off assist behavior is lessened, thereby giving the user more control over the movement of the joint. As another option, the toe-off assist behavior may be delayed or be configured to move slower etc.

In some cases, swing phase behavior of a traditional active POD can modified such that the controllers operates in a passive mode and does not contribute with any power injection. In some cases, operating the controller in passive mode during swing phase can allow the user to be in full control of the POD operation.

In some cases, the controller 226 can determine which mode to operate in based on one or more gait parameters. For example, the selected controller mode can be based on the dynamic evaluation of a gait parameter.

If a user has not taken a step for a predetermined amount of time, the controller 226 can determine that the user is standing and can select a passive mode. In the passive mode, the POD can act like a passive POD. For example, in the passive mode, the controller can cause the actuator to exhibit FR behavior during stance phase and FF behavior during swing phase. In certain embodiments, in passive mode, the actuator may not exhibit a toe-off assist behavior during stance phase. As described herein during a FF behavior, the active POD can detect an amount of torque applied to it from the user and use the motor of the active POD to apply that same amount of torque in the same direction with some additional torque to overcome the internal resistance of the joint itself. In this way, the joint can be made to feel like a free swinging joint to the user with little to no resistance. During a FR sub-phase (during stance phase), the active POD can detect an amount of torque applied to it from the user (for example, weight of the user) and use the motor of the active POD to apply that same amount of torque to the joint in the opposite direction. In this way, the joint can be made to feel stable without much if any give to the user.

As another example, if the user takes multiple steps, a large step (measured for example, based on absolute thigh angle, absolute shank angle) or the active POD detects a larger amount of force on the toe than usual, or a particular gait parameter satisfies a gait parameter threshold, the controller 226 can transition to an active mode. In the active mode, the active POD can actively move the joint or include additional sub-phases. For example, in active mode, the POD can include a toe-off assist behavior during stance phase (following a FR sub-phase) where the joint is flexed in preparation for a toe-off event, as described herein, and as shown in FIG. 7.

Non-Limiting Examples

To illustrate the hybrid control more operation, consider the standing to walking management, where the number of steps completed on the prosthetic limb from the last standing position is the gait parameter.

Figures 8A, 8B, 8C:
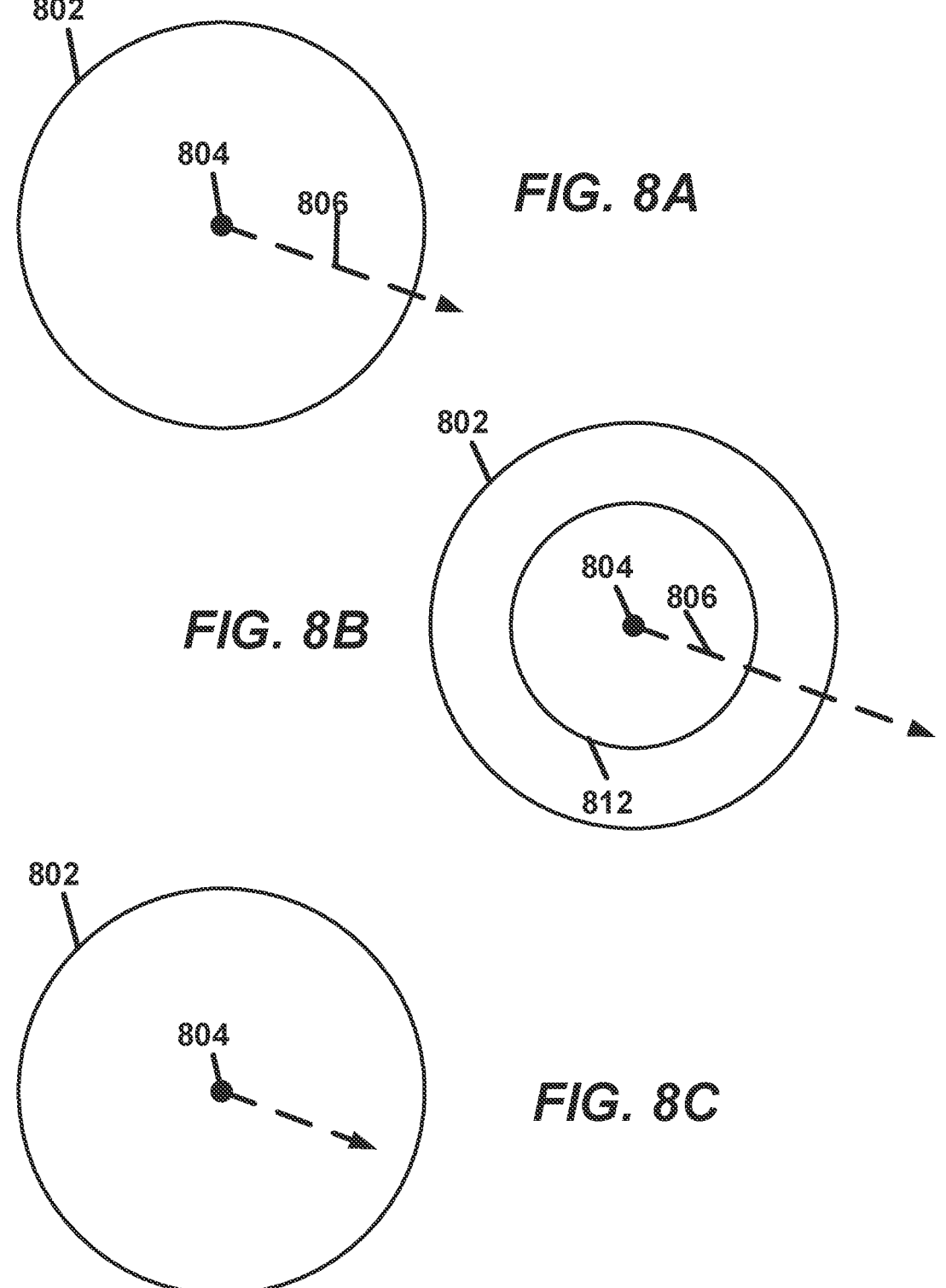
FIGS. 8A-8C depict various illustrative examples of operational maps for a hybrid control scheme for a POD.

FIGS. 8A-8C depict various illustrative examples of operational maps for a hybrid control scheme for a POD. FIG. 8A depicts an example of an operational map where two operational sub-spaces (the area inside the circle 802 and the area outside the circle 802) are used to manage the actuator behavior as the user progresses in the operational environment. In the illustrative example, the circle 802 represents a gait parameter threshold, and the location of the point 804 relative to the outer circle 802 represents whether the gait parameter threshold is satisfied. That is, the gait parameter threshold is not satisfied while the point 804 (extending along arrow 806) is within the outer circle 802 and the gait parameter threshold is satisfied when the point 804 (extending along arrow 806) is located on or outside the circle 802. In certain cases, the circle 802 may also represent the transition between modes and/or activities. For example, inside circle 802 can represent the passive mode and/or a standing activity and outside circle 802 can represent the active mode and/or a walking activity. Thus, in the illustrated embodiment of FIG. 8A, transitioning from a passive mode to an active mode can coincide with transitioning from a standing activity to a walking activity.

As a non-limiting example, and with specific reference to FIG. 8A, as the user remains within the circle 802, the gait parameter threshold is not satisfied and the controller management scheme can use the passive mode, as described herein at least with reference to FIG. 6. As the gait parameter satisfies the gait parameter threshold (in this example, the user completes two side steps), the user transitions to the second sub-space (outside of the circle 802), and the controller is dynamically reconfigured to operate in the active mode and transitions to a walking activity. For example, as the user begins to move, the controller 226 (for example, using the inference layer) determines that the gait parameter threshold is satisfied and can change the activity from "standing" to "walking." The controller 226 (for example, using the reactive layer) is then configured to implement a walking management scheme. In addition, based on a determination that the gait parameter threshold is satisfied, the controller (e.g., using the inference layer) can transition to an active mode.

FIG. 8C illustrates the evolution of a user who does not complete transition from the first sub-space (the area inside the circle 802) to the second sub-space (the area outside the circle 812) when operating in a two sub-spaces hybrid control scheme. As an example, FIG. 8C can represent a case where the user started moving in the operational parameter map, but stopped before reaching the gait parameter threshold to operate in active mode. In this case, the user would have operated in the passive mode for the complete evolution represented.

FIG. 8B illustrates a hybrid control scheme using three sub-spaces: the area inside the circle 812, the area inside circle 802 and outside circle 812, and the area outside the circle 802. Similar to FIGS. 8A and 8B, the circle 802 can represent a gait parameter threshold. In addition, the circle 812 can represent another gait parameter threshold. Thus, the operational maps for the hybrid control scheme in FIG. 8B can include a first gait parameter threshold (corresponding to circle 812) used to transition between the first sub-space and the second sub-space and a second gait parameter threshold (corresponding to circle 802) used to transition between the second sub-space and the third sub-space.

In this case, operation can be similar to the hybrid control scheme of FIGS. 8A and 8C, but use of higher number of sub-spaces allows for more refined progression of the actuator behavior. As the user completes the two prosthetic side steps (e.g., satisfies the first gait parameter threshold) and transitions to the second sub-space (the area inside circle 802 and outside circle 812), the controller selects active mode and dynamically reconfigures the impedance controller gains values such that the toe-off assist behavior, brake behavior, and the bumper avoidance behavior (e.g., and/or other actively modified joint behaviors) are operating in reduced power (for example, half power). In such a scenario, however, transitioning to the second sub-space or the active mode may not result in the prosthetic changing its activity state (e.g., from "standing" to "walking"). Instead, the POD may remain in a standing activity state, but in an active mode, as described herein at least with reference to FIG. 7. As the user progresses in the operational variable space and transitions to the third sub-space (the area outside circle 802) after completing 4 steps on the POD (e.g., satisfies the second gait parameter threshold), the reactive layer further updates the impedance controller gain values to operating in the full active mode such that the toe-off assist behavior, brake behavior, and the bumper avoidance behavior are operating at full power. In addition, upon transitioning to the third sub-space, the inference layer may transition the POD from a standing activity state to a walking activity state. In certain cases, the inference layer may not transition the POD from the standing activity state to the walking activity state based on the transition to the third sub-space. In some such cases, additional gait parameter thresholds (and/or sub-spaces) may be used to determine when to transition from the standing activity state to the walking activity state.

Similarly, within the standing activity (or any other activity of the POD), there may be multiple sub-spaces and/or gait parameter thresholds used to activate and/or adjust the power levels of one or more actively modified joint behaviors.

Accordingly, the sub-spaces of the hybrid control scheme (e.g., the second sub-space on FIG. 8B), the passive/active modes, the different actively modified joint behaviors within the active mode, and/or the different power levels of actively modified joint behaviors within the active mode can provide flexible and dynamic phases between discrete controller states, thereby smoothing the transition between discreet activities (e.g., standing and walking) in a physiologically compliant way. In this manner, the hybrid control mode can improve the usability and functionality of a POD for a user.

Non-Motorized POD

Although the present disclosure is generally described with respect to a motorized POD, the teachings may be applied to semi-active or non-motorized PODs as well, such as a magnetorheological (MR) knee.

Figure 9:
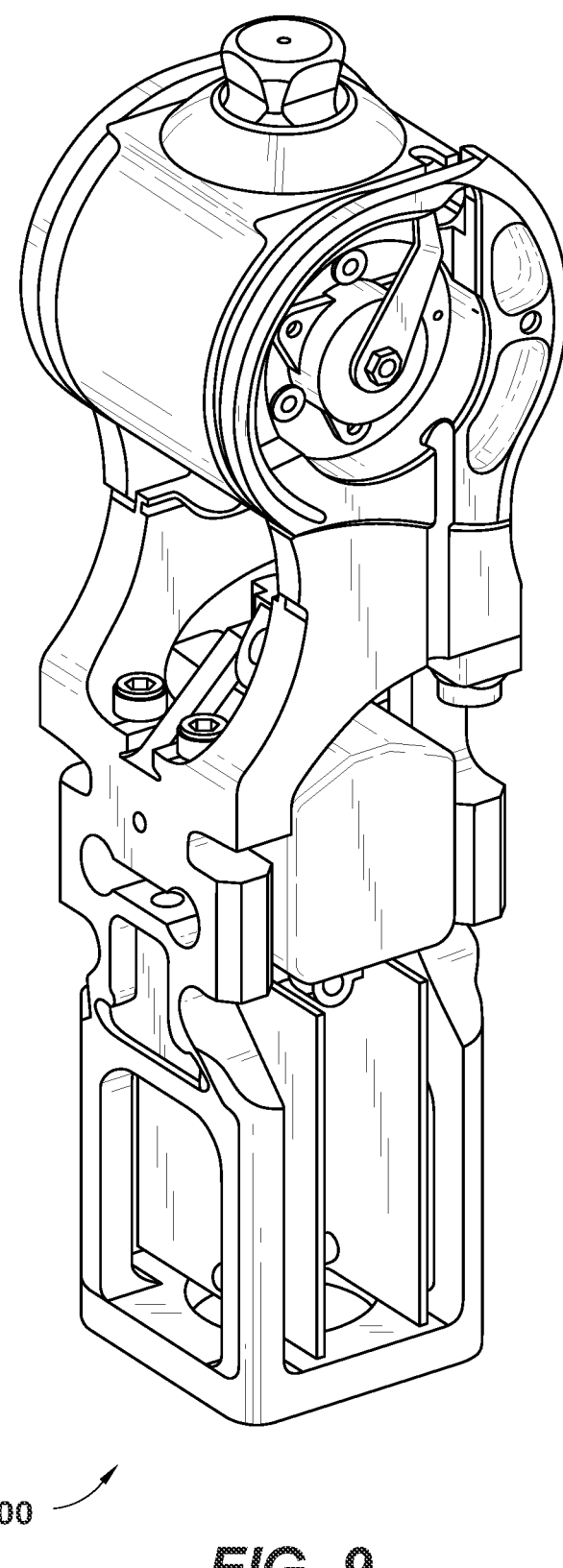
FIG. 9 illustrates a block diagram of a non-motorized POD.

FIG. 9 illustrates an example POD 900 that includes a controller and an actuator. The actuator can be implemented as a rotary MR knee actuator that includes MR fluid. MR fluid is a field responsive (FR) fluid or medium that undergoes a rheology or viscosity change which is dependent on the magnitude of an applied magnetic field. This variation in fluid viscosity can control a magnitude of the shearing force/stress, torque or torsional resistance generated, and hence the level of damping provided by the knee actuator and/or the prosthetic knee.

As described herein, the controller can include at least two controller modes: an active mode and a passive mode. Depending on the controller mode, the controller can determine whether to apply resistance to the knee and, if so, how much resistance to provide. Although implemented differently, the POD 900 can include behaviors and modes that are similar to the behaviors and modes described above with reference to POD 100. For example, the POD 900 can include or implement a force rejection behavior, force following behavior, toe-off assist behavior, braking assist and bumper avoidance. As the POD 900 may not have a motor, implementing the various behaviors and modes may be done by increasing or decreasing the resistance of the joint.

The increase/decrease of the resistance or resistive braking effect at the knee joint can be a function of the MR fluid viscosity, which in turn is a function of the magnetic field. In some cases, the controller of the POD 900 passes a variable, controlled current through a coil, which creates the variable magnetic field. Thus, by controlling the current through the coil, the magnitude of the magnetic field is controlled, thereby controlling the POD's resistance to rotary motion. The controller can increase the resistance at the knee joint by increasing the current through the coil and/or increasing the magnetic field. Similarly, the controller can decrease the resistance at the knee joint by decreasing the current through the coil and/or decreasing the magnetic field.

In passive mode, the controller can cause the POD 900 to mimic or correspond to a passive POD using a force rejection behavior and a force following behavior. In some cases, the POD 900 can implement the force rejection behavior by applying the resistive braking effect to the knee during at least a portion of stance phase. In certain cases, the controller can cause the POD to apply the resistive braking effect during the entire stance phase. In some cases, the controller can vary the resistive braking effect based on a determined torque at the knee joint and/or a determined velocity at the knee joint. For example, the controller can vary the resistive braking effect in proportion to the determined torque and/or determined velocity at the knee joint (e.g., increase/decrease as the determined torque and/or determined velocity increases/decreases).

Furthermore, in passive mode, during swing phase, the controller can cause the actuator to be compliant and free to flex under the loading imposed by the user and its interaction with the environment (e.g., as the user swing the POD forward). To do so, the controller can decrease or remove the resistive braking effect or reduce or remove resistance during swing phase, which can allow the POD to move or swing more freely or easily. As described herein, the controller can reduce or remove resistance by decreasing the current through the coil, thereby decreasing the variable magnetic field and the MR fluid viscosity.

In active mode, the controller can cause the POD 900 to facilitate the stance and swing phases using different actively modified joint behaviors as shown and described above with reference to FIG. 7. As mentioned, the actively modified joint behaviors of the POD 900 may be similar to the actively modified joint behaviors of the POD 100 in that they increase or decrease resistance at different portions of the stance and swing, however, as the POD 900 is not motorized, it may not actively move the limb members relative to each other. Instead, the actively modified joint behaviors of the POD 900 may reflect increases/decreases in the amount of resistance at the joint. Furthermore, the descriptions herein with respect to activating some or all actively modified joint behaviors concurrently or sequentially (e.g., based on different gait parameter thresholds), varying the amount of power used for the actively modified joint behaviors (e.g., based on different gait parameter thresholds or values), can be applied to the POD 900.

In certain cases, in the active mode, the controller can cause the POD 900 to provide a toe-off assist behavior during at least a portion of the stance phase. For example, in some cases, the controller can cause the actuator to reduce a resistance of the POD 900 during a portion of the stance phase. In some cases, the toe-off assist behavior may be implemented near the end of stance phase and may follow a force rejection behavior, as illustrated and described in FIG. 7. Reducing the resistance of the POD can facilitate flexion of the knee while the foot is still in contact with the ground. In some cases, the toe-off assist behavior or this reduction in resistance can extend from midstance until toe-off.

As another example, in active mode, the controller can cause the actuator to increase in resistance at the joint during a first portion of the stance phase, decrease in resistance at the joint during a second portion of the stance phase, decrease in resistance at the joint during at least a first portion of the swing phase, increase in resistance at the joint to decelerate flexion of the POD during at least a second portion of the swing phase, and increase in resistance at a third portion of the swing phase to decelerate extension of the POD during at least a third portion of the swing phase.

As another example, in active mode, the controller can cause the actuator to increase a resistance of the POD 900 during portions of the swing phase. For instance, the controller can cause the actuator to apply a resistive braking effect to decelerate flexion of the knee (e.g., analogous in at least some respects to the braking behavior described above with reference to POD 100) or decelerate extension of the knee (e.g., analogous in at least some respects to the bumper avoidance behavior described above with reference to POD 100). For example, as part of a braking behavior, the controller can control the actuator to decelerate flexion of the knee until the heel reaches a second heel rise target based on a determination that a heel associated with the knee has reached a first heel rise target. As another example, as part of a bumper avoidance behavior, the controller can control the actuator to decelerate extension of the knee until the heel reaches a second heel rise target based on a determination that a heel associated with the knee has reached a first heel rise target. The first heel rise target can occur during the Initial Swing subphase. For example, the first heel rise target can occur between toe-off and maximum knee flexion. The first knee extension target can occur after maximum knee flexion during swing phase (e.g., during mid swing).

As shown and described above, at least with reference to FIGS. 6 and 7, the various behaviors and actively modified joint behaviors can be used during different portions of the stance phase and swing phase to improve the gait of the user.

The POD 900 can include one or more different or additional components or features, such as those described in greater detail in U.S. Pub. No. 2001/0029400, filed Jan. 22, 2001, entitled "ELECTRONICALLY CONTROLLED PROSTHETIC KNEE," U.S. Pub. No. 2005/0283257, filed Mar. 9, 2005, entitled "CONTROL SYSTEM AND METHOD FOR A PROSTHETIC KNEE," or U.S. Pub. No. 2006/0074493, filed May 6, 2005, entitled "SYSTEMS AND METHODS OF LOADING FLUID IN A PROSTHETIC KNEE," each of which is hereby incorporated by reference in its entirety and includes concepts that are compatible with and can be used in conjunction with any combination of the embodiments and/or features described herein.

EXAMPLE EMBODIMENTS

Various example embodiments of apparatuses, methods, and systems relating to dynamically implementing actively modified joint behavior to a user of an active or semi-active POD can be found in the following clauses:

Clause 1. A powered prosthetic knee, comprising:

a first limb member;

a second limb member coupled to the first limb member at a joint;

a motorized actuator coupled to the first limb member and the second limb member and configured to actuate the first limb member relative to the second limb member;

a sensor module configured to obtain gait parameter data associated with the powered prosthetic knee; and a controller communicatively coupled to the actuator, the controller configured to:

receive the gait parameter data from the sensor module, select a controller mode based at least in part on the gait parameter data, and based on the selected controller mode, communicate one or more command signals to the actuator, wherein based on a determination that a gait parameter does not satisfy a gait parameter threshold, the controller selects a passive mode for the controller mode, wherein in the passive mode, the controller causes the actuator to exhibit a force rejection behavior during at least a portion of stance phase and exhibit a force following behavior during at least a portion of swing phase, and wherein based on a determination that the gait parameter satisfies the gait parameter threshold, the controller selects an active mode for the controller mode, wherein in the active mode, the controller causes the actuator to exhibit the force rejection behavior and exhibit a force following behavior during swing and at least one behavior of a toe-off assist behavior during at least a portion of the stance phase, a braking behavior during at least a portion of the swing phase, or a bumper avoidance behavior during at least a portion of the swing phase.

Clause 2. The powered prosthetic knee of clause 1, wherein the controller causes the actuator to exhibit the toe-off assist behavior during at least a portion of the stance phase, the braking behavior during at least a portion of the swing phase, and the bumper avoidance behavior during at least a portion of the swing phase based on the determination that the gait parameter satisfies the gait parameter threshold.

Clause 3. The powered prosthetic knee of any of the previous clauses, wherein the controller causes the actuator to exhibit at least two behaviors of the toe-off assist behavior, the braking behavior, and the bumper avoidance behavior based on a determination that the gait parameter satisfies the gait parameter threshold.

Clause 4. The powered prosthetic knee of any of the previous clauses, wherein the gait parameter threshold is a first gait parameter threshold, wherein the controller causes the actuator to exhibit the toe-off assist behavior, the braking behavior, and the bumper avoidance behavior based on a determination that the gait parameter satisfies a second gait parameter threshold.

Clause 5. The powered prosthetic knee of any of the previous clauses, wherein the gait parameter threshold is a first gait parameter threshold, wherein the controller causes the actuator to exhibit at least two behaviors of the toe-off assist behavior, the braking behavior, and the bumper avoidance behavior based on a determination that the gait parameter satisfies a second gait parameter threshold.

Clause 6. The powered prosthetic knee of any of the previous clauses, wherein the controller causes the actuator to exhibit at least one behavior of the toe-off assist behavior, the braking behavior, and the bumper avoidance behavior at a maximum power level based on the determination that the gait parameter satisfies the gait parameter threshold.

Clause 7. The powered prosthetic knee of any of clauses 1-5, wherein the controller causes the actuator to exhibit at least one behavior of the toe-off assist behavior, the braking behavior, and the bumper avoidance behavior at a power level based on the determination that the gait parameter satisfies the gait parameter threshold, and wherein the power level varies in proportion with the gait parameter.

Clause 8. The powered prosthetic knee of any of clauses 1-5, wherein the gait parameter threshold is a first gait parameter threshold, wherein the controller causes the actuator to:
exhibit the at least one behavior at a first power level based on the determination that the gait parameter satisfies the first gait parameter threshold, and
exhibit the at least one behavior at a second power level based on a determination that the gait parameter satisfies a second gait parameter threshold.

Clause 9. The powered prosthetic knee of any of the previous clauses, wherein the gait parameter threshold is a first gait parameter threshold, and wherein the controller causes the actuator to:
exhibit a first behavior of at least one of toe-off assist behavior, the braking behavior, and the bumper avoidance behavior at a first power level based on a determination that the gait parameter satisfies the gait parameter threshold,
exhibit a second behavior of at least one of the toe-off assist behavior, the braking behavior, and the bumper avoidance behavior at a second power level based on a determination that the gait parameter satisfies a second gait parameter threshold, wherein the second power level varies in proportion with the gait parameter.

Clause 10. The powered prosthetic knee of any of the previous clauses, wherein the controller causes the actuator to:
exhibit the braking behavior and the bumper avoidance behavior at a first power level based on a determination that the gait parameter satisfies the gait parameter threshold,
exhibit the toe-off assist behavior at a second power level that is lower than the first power level based on a determination that the gait parameter satisfies a second gait parameter threshold, wherein the second power level varies in proportion to the gait parameter.

Clause 11. The powered prosthetic knee of any of the preceding clauses, wherein the controller is further configured to determine a first torque at the joint, and wherein to cause the actuator to exhibit the force rejection behavior, the controller causes the actuator to apply a second torque at the joint, wherein the second torque is equal to and opposite the first torque, and wherein the first torque corresponds to a force applied to the powered prosthetic knee by the user.

Clause 12. The powered prosthetic knee of any of the preceding clauses, wherein in the active mode, the actuator exhibits the force rejection behavior during at least a portion of the stance phase between foot strike and midstance.

Clause 13. The powered prosthetic knee of any of the preceding clauses, wherein the controller is further configured to determine a first torque at the joint applied to the joint by a user, and wherein to cause the actuator to exhibit the force following behavior, the controller causes the actuator to apply a second torque at the joint, wherein the second torque is in the same direction as the first torque.

Clause 14. The powered prosthetic knee of any of clauses 11-13, wherein the second torque is greater than or equal to the first torque.

Clause 15. The powered prosthetic knee of any of clauses 11-13, wherein the second torque is equal to a sum of the first torque and a third torque, wherein the third torque is based on an internal resistance of the joint.

Clause 16. The powered prosthetic knee of any of the preceding clauses, wherein in the active mode, the controller causes the actuator to exhibit the force following behavior during at least a portion of the swing phase between toe off and a heel rise target.

Clause 17. The powered prosthetic knee of any of the preceding clauses, wherein to cause the actuator to exhibit the toe-off assist behavior, the controller controls the actuator to apply a torque at the joint to cause the powered prosthetic knee to flex.

Clause 18. The powered prosthetic knee of any of the preceding clauses, wherein in the active mode, the controller causes the actuator to exhibit the toe-off assist behavior during at least a portion of the stance phase between midstance and toe off Clause 19. The powered prosthetic knee of any of the preceding clauses, wherein in the active mode, the controller is configured to:
based on a determination that a heel associated with the powered prosthetic knee has reached a first heel rise target, control the actuator to decelerate flexion of the powered prosthetic knee until the heel reaches a second heel rise target.

Clause 20. The powered prosthetic knee of clause 19, wherein the second heel rise target corresponds to a maximum flexion of the powered prosthetic knee during the swing phase.

Clause 21. The powered prosthetic knee of any of clause 19 or 20, wherein in the active mode, the controller is configured to:

based on a determination that the heel has reached the second heel rise target, cause the actuator to exhibit the force following behavior.

Clause 22. The powered prosthetic knee of any of the preceding clauses, wherein in the active mode, the controller is configured to:

based on a determination that a knee angle satisfies a first knee extension target, control the actuator to decelerate extension of the joint until the knee reaches a second knee extension target.

Clause 23. The powered prosthetic knee of clause 22, wherein the knee extension target corresponds to a maximum extension of the powered prosthetic knee during the swing phase.

Clause 24. The powered prosthetic knee of any of the preceding clauses, wherein the gait parameter data corresponds to a gait parameter, wherein the gait parameter comprises at least one of user forward speed, walking cadence, stance time, thigh angle excursion amplitude during stance phase, absolute thigh angle at toe-off, absolute thigh angle at foot strike, knee torque amplitude at late stance, number of steps completed while achieving a minimum swing flexion amplitude, thigh or shank sagittal plane rotational or linear acceleration, thigh or shank sagittal plane rotational speed amplitude, ground reaction force amplitude at foot strike, ground reaction force amplitude on toe in late stance, user center of mass linear acceleration, a ground interaction, a shank angle, or a joint angle.

Clause 25. The powered prosthetic knee of any of the preceding clauses, wherein based on a determination that the gait parameter satisfies the gait parameter threshold, the controller selects the active mode for the controller mode.

Clause 26. The powered prosthetic knee of any of the preceding clauses, wherein the controller mode transitions from the active mode to the passive mode based at least in part on a determination that the gait parameter satisfies the gait parameter threshold.

Clause 27. The powered prosthetic knee of any of the preceding clauses, wherein based on a determination that the user is starting to walk or has changed locations, the controller selects the active mode for the controller mode.

Clause 28. The powered prosthetic knee of any of the preceding clauses, wherein the controller mode transitions from the passive mode to the active mode based at least in part on a determined activity of the user.

Clause 29. A prosthetic or orthotic device comprising:
a first limb member;
a second limb member coupled to the first limb member at a joint;
an actuator coupled to the first limb member and the second limb member and configured to actuate the first limb member relative to the second limb member; and
a controller configured to control the actuator, the controller further configured to:
based at least in part on a determination that a first gait parameter does not satisfy a first gait parameter threshold, select a passive mode for the controller mode, wherein in the passive mode, the controller causes the actuator to exhibit a force rejection behavior during at least a portion of stance phase and exhibits a force following behavior during at least a portion of swing phase, and
based at least in part on a determination that the first gait parameter satisfies the first gait parameter threshold, select an active mode for the controller mode, wherein in the active mode, the controller:
causes the actuator to exhibit a force rejection behavior during at least a portion of stance phase and exhibit a force following behavior during at least a portion of swing phase, and
dynamically activates at least one of a toe-off assist behavior, a braking behavior, or a bumper avoidance behavior.

Clause 30. The prosthetic or orthotic device of clause 29, wherein the controller causes the actuator to exhibit the toe-off assist behavior during at least a portion of the stance phase, the braking behavior during at least a portion of the swing phase, and the bumper avoidance behavior during at least a portion of the swing phase based on the determination that the gait parameter satisfies the gait parameter threshold.

Clause 31. The prosthetic or orthotic device of any of clauses 29 or 30, wherein the controller causes the actuator to exhibit at least two behaviors of the toe-off assist behavior, the braking behavior, and the bumper avoidance behavior based on a determination that the gait parameter satisfies the gait parameter threshold.

Clause 32. The prosthetic or orthotic device of any of clauses 29-31, wherein the gait parameter threshold is a first gait parameter threshold, wherein the controller causes the actuator to exhibit the toe-off assist behavior, the braking behavior, and the bumper avoidance behavior based on a determination that the gait parameter satisfies a second gait parameter threshold.

Clause 33. The prosthetic or orthotic device of any of clauses 29-32, wherein the gait parameter threshold is a first gait parameter threshold, wherein the controller causes the actuator to exhibit at least two behaviors of the toe-off assist behavior, the braking behavior, and the bumper avoidance behavior based on a determination that the gait parameter satisfies a second gait parameter threshold.

Clause 34. The prosthetic or orthotic device of any of clauses 29-33, wherein the controller causes the actuator to exhibit at least one behavior of the toe-off assist behavior, the braking behavior, and the bumper avoidance behavior at a maximum power level based on the determination that the gait parameter satisfies the gait parameter threshold.

Clause 35. The prosthetic or orthotic device of any of clauses 29-34, wherein the controller causes the actuator to exhibit at least one behavior of the toe-off assist behavior, the braking behavior, and the bumper avoidance behavior at a power level based on the determination that the gait parameter satisfies the gait parameter threshold, and wherein the power level varies in proportion with the gait parameter.

Clause 36. The prosthetic or orthotic device of any of clauses 29-35, wherein the gait parameter threshold is a first gait parameter threshold, wherein the controller causes the actuator to:
exhibit the at least one behavior at a first power level based on the determination that the gait parameter satisfies the first gait parameter threshold, and
exhibit the at least one behavior at a second power level based on a determination that the gait parameter satisfies a second gait parameter threshold.

Clause 37. The prosthetic or orthotic device of any of clauses 29-36, wherein the gait parameter threshold is a first gait parameter threshold, and wherein the controller causes the actuator to:

exhibit a first behavior of at least one of toe-off assist behavior, the braking behavior, and the bumper avoidance behavior at a first power level based on a determination that the gait parameter satisfies the gait parameter threshold, exhibit a second behavior of at least one of the toe-off assist behavior, the braking behavior, and the bumper avoidance behavior at a second power level based on a determination that the gait parameter satisfies a second gait parameter threshold, wherein the second power level varies in proportion with the gait parameter.

Clause 38. The prosthetic or orthotic device of any of clauses 29-37, wherein the controller causes the actuator to:

exhibit the braking behavior and the bumper avoidance behavior at a first power level based on a determination that the gait parameter satisfies the gait parameter threshold, exhibit the toe-off assist behavior at a second power level that is lower than the first power level based on a determination that the gait parameter satisfies a second gait parameter threshold, wherein the second power level varies in proportion to the gait parameter.

Clause 39. A prosthetic or orthotic device (POD) comprising:

a first limb member;

a second limb member coupled to the first limb member at a joint;

an actuator coupled to the first limb member and the second limb member and configured to actuate the first limb member relative to the second limb member; and a controller configured to control the actuator, the controller further configured to:

cause the actuator to exhibit a force rejection behavior during at least a portion of stance phase, cause the actuator to exhibit a force following behavior during at least a portion of swing phase, and based on a determination that a first gait parameter satisfies a first gait parameter threshold, further cause the actuator to at least one of: apply a first torque at the joint to cause the POD to flex during at least a portion of stance phase, decelerate flexion of the POD during at least a first portion of the swing phase or decelerate extension of the POD during at least a second portion of the swing phase.

Clause 40. The prosthetic or orthotic device of clause 39, wherein:

based on a determination that the first gait parameter satisfies the gait parameter threshold, the controller is further configured to control the actuator to apply the first torque to the joint to cause the POD to flex between midstance and toe-off, and based on a determination that the first gait parameter satisfies a second gait parameter threshold and the third gait parameter threshold, the controller is further configured to control the actuator to apply a second torque to the joint to cause the POD to flex between midstance and toe-off, wherein the second torque is greater than the first torque.

Clause 41. The prosthetic or orthotic device of any of clauses 39 or 40, wherein the controller causes the actuator to exhibit the toe-off assist behavior during at least a portion of the stance phase, the braking behavior during at least a portion of the swing phase, and the bumper avoidance behavior during at least a portion of the swing phase based on the determination that the gait parameter satisfies the gait parameter threshold.

Clause 42. The prosthetic or orthotic device of any of clauses 39-41, wherein the controller causes the actuator to exhibit at least two behaviors of the toe-off assist behavior, the braking behavior, and the bumper avoidance behavior based on a determination that the gait parameter satisfies the gait parameter threshold.

Clause 43. The prosthetic or orthotic device of any of clauses 39-42, wherein the gait parameter threshold is a first gait parameter threshold, wherein the controller causes the actuator to exhibit the toe-off assist behavior, the braking behavior, and the bumper avoidance behavior based on a determination that the gait parameter satisfies a second gait parameter threshold.

Clause 44. The prosthetic or orthotic device of any of clauses 39-43, wherein the gait parameter threshold is a first gait parameter threshold, wherein the controller causes the actuator to exhibit at least two behaviors of the toe-off assist behavior, the braking behavior, and the bumper avoidance behavior based on a determination that the gait parameter satisfies a second gait parameter threshold.

Clause 45. The prosthetic or orthotic device of any of clauses 39-44, wherein the controller causes the actuator to exhibit at least one behavior of the toe-off assist behavior, the braking behavior, and the bumper avoidance behavior at a maximum power level based on the determination that the gait parameter satisfies the gait parameter threshold.

Clause 46. The prosthetic or orthotic device of any of clauses 39-45, wherein the controller causes the actuator to exhibit at least one behavior of the toe-off assist behavior, the braking behavior, and the bumper avoidance behavior at a power level based on the determination that the gait parameter satisfies the gait parameter threshold, and wherein the power level varies in proportion with the gait parameter.

Clause 47. The prosthetic or orthotic device of any of clauses 39-46, wherein the gait parameter threshold is a first gait parameter threshold, wherein the controller causes the actuator to:

exhibit the at least one behavior at a first power level based on the determination that the gait parameter satisfies the first gait parameter threshold, and exhibit the at least one behavior at a second power level based on a determination that the gait parameter satisfies a second gait parameter threshold.

Clause 48. The prosthetic or orthotic device of any of clauses 39-47, wherein the gait parameter threshold is a first gait parameter threshold, and wherein the controller causes the actuator to:

exhibit a first behavior of at least one of toe-off assist behavior, the braking behavior, and the bumper avoidance behavior at a first power level based on a determination that the gait parameter satisfies the gait parameter threshold, exhibit a second behavior of at least one of the toe-off assist behavior, the braking behavior, and the bumper avoidance behavior at a second power level based on a determination that the gait parameter satisfies a second gait parameter threshold, wherein the second power level varies in proportion with the gait parameter.

Clause 49. The prosthetic or orthotic device of any of clauses 39-48, wherein the controller causes the actuator to:

exhibit the braking behavior and the bumper avoidance behavior at a first power level based on a determination that the gait parameter satisfies the gait parameter threshold, exhibit the toe-off assist behavior at a second power level that is lower than the first power level based on a determination that the gait parameter satisfies a second gait parameter threshold, wherein the second power level varies in proportion to the gait parameter.

Clause 50. A prosthetic or orthotic device comprising:

a joint; and a controller configured to:

receive the gait parameter data; and select an active mode or a passive mode based at least in part on the gait parameter data;

wherein in the passive mode, the controller causes an increase in resistance at the joint during stance phase and causes a decrease in resistance at the joint during swing phase, and wherein in the active mode, the controller causes:

an increase in resistance at the joint during a first portion of the stance phase, a decrease in resistance at the joint during a second portion of the stance phase, a decrease in resistance at the joint during at least a first portion of the swing phase, an increase in resistance at the joint to decelerate flexion of the POD during at least a second portion of the swing phase, and an increase in resistance at a third portion of the swing phase to decelerate extension of the POD during at least a third portion of the swing phase.

Clause 51. The prosthetic or orthotic device of clause 50, wherein the actuator is a non-motorized actuator, and wherein the controller causes an increase in resistance by increasing a resistive braking effect.

Clause 52. The prosthetic or orthotic device of any of clauses 50 or 51, wherein the actuator is a non-motorized actuator, and wherein the controller causes a decrease in resistance by decreasing a resistive braking effect.

Clause 53. The prosthetic or orthotic device of any of clauses 50-52, wherein the actuator is a magnetorheological fluid actuator.

Clause 54. The prosthetic or orthotic device of clause 50, wherein the actuator is a motorized actuator, and wherein the controller causes an increase in resistance by causing the actuator to apply torque to the joint in opposite direction of a determined torque at the joint.

Clause 55. The prosthetic or orthotic device of any of clauses 50 and 54, wherein the actuator is a motorized actuator, and wherein the controller causes a decrease in resistance by causing an actuator to apply torque to the joint to apply torque in same direction as a determined velocity of the joint.

Clause 56. A method of operating the powered prosthetic knee of any of clauses 1-28.

Clause 57. A method of operating the prosthetic or orthotic device of any of clauses 29-55.

Clause 58. A method of operating the prosthetic or orthotic device of any of clauses 29-55.

Clause 59. A prosthetic or orthotic device comprising one or more features of the foregoing description and/or figures.

Clause 60. A method of operating a prosthetic or orthotic device comprising one or more features of the foregoing description and/or accompanying figures.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may include, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic or orthotic device comprising:
a first limb member;
a second limb member coupled to the first limb member at a joint;
an actuator coupled to the first limb member and the second limb member and configured to actuate the first limb member relative to the second limb member; and
a controller configured to control the actuator, the controller further configured to:
based at least in part on a determination that a gait parameter does not satisfy a gait parameter threshold, select a passive mode for a controller mode of the controller, wherein in the passive mode, the controller causes the actuator to exhibit a force rejection behavior during at least a portion of stance phase and exhibits a force following behavior during at least a portion of swing phase, and
based at least in part on a determination that the gait parameter satisfies the gait parameter threshold, select an active mode for the controller mode, wherein in the active mode, the controller:
causes the actuator to exhibit a force rejection behavior during at least a portion of stance phase and exhibit a force following behavior during at least a portion of swing phase, and
causes the actuator to exhibit at least one of a toe-off assist behavior, a braking behavior, or a bumper avoidance behavior at a power level, wherein the power level varies in proportion with the gait parameter.

2. The prosthetic or orthotic device of claim 1, wherein the controller causes the actuator to exhibit at least two behaviors of the toe-off assist behavior, the braking behavior, and the bumper avoidance behavior based on a determination that the gait parameter satisfies the gait parameter threshold.

3. The prosthetic or orthotic device of claim 1, wherein the gait parameter threshold is a first gait parameter threshold, wherein the controller causes the actuator to exhibit at least two behaviors of the toe-off assist behavior, the braking behavior, and the bumper avoidance behavior based on a determination that the gait parameter satisfies a second gait parameter threshold.

4. The prosthetic or orthotic device of claim 1, wherein the gait parameter threshold is a first gait parameter threshold, wherein the controller causes the actuator to:
exhibit at least one behavior of the toe-off assist behavior, the braking behavior, and the bumper avoidance behavior at a first power level based on the determination that the gait parameter satisfies the first gait parameter threshold, and
exhibit at least one behavior of the toe-off assist behavior, the braking behavior, and the bumper avoidance behavior at a second power level based on a determination that the gait parameter satisfies a second gait parameter threshold.

5. The prosthetic or orthotic device of claim 1, wherein the controller is further configured to determine a first torque at the joint, and wherein to cause the actuator to exhibit the force rejection behavior, the controller causes the actuator to apply a second torque at the joint, wherein the second torque is equal to and opposite the first torque, and wherein the first torque corresponds to a force applied to the prosthetic or orthotic device by a user.

6. The prosthetic or orthotic device of claim 1, wherein in the active mode, the actuator exhibits the force rejection behavior during at least a portion of the stance phase between foot strike and midstance.

7. The prosthetic or orthotic device of claim 1, wherein the controller is further configured to determine a first torque at the joint applied to the joint by a user, and wherein to cause the actuator to exhibit the force following behavior, the controller causes the actuator to apply a second torque at the joint, wherein the second torque is in a same direction as the first torque.

8. The prosthetic or orthotic device of claim 1, wherein in the active mode, the controller causes the actuator to exhibit the force following behavior during at least a portion of the swing phase between toe off and a heel rise target.

9. The prosthetic or orthotic device of claim 1, wherein in the active mode, wherein the controller causes the actuator to exhibit the toe-off assist behavior, the toe-off assist behavior occurs during at least a portion of the stance phase between midstance and toe off.

10. The prosthetic or orthotic device of claim 1, wherein in the active mode, the controller is configured to:
based on a determination that a heel associated with the prosthetic or orthotic device has reached a first heel rise target, control the actuator to decelerate flexion of the prosthetic or orthotic device until the heel reaches a second heel rise target.

11. The prosthetic or orthotic device of claim 10, wherein in the active mode, the controller is configured to:
based on a determination that the heel has reached the second heel rise target, cause the actuator to exhibit the force following behavior.

12. The prosthetic or orthotic device of claim 1, wherein the prosthetic or orthotic device is a powered knee, and wherein in the active mode, the controller is configured to:
based on a determination that a knee angle satisfies a first knee extension target, control the actuator to decelerate extension of the joint until the powered knee reaches a second knee extension target.

13. The prosthetic or orthotic device of claim 1, wherein the prosthetic or orthotic device comprises of a sensor module configured to obtain gait parameter data associated with the prosthetic or orthotic device, and wherein the gait parameter data corresponds to a gait parameter, wherein the gait parameter comprises at least one of user forward speed, walking cadence, stance time, thigh angle excursion amplitude during stance phase, absolute thigh angle at toe-off, absolute thigh angle at foot strike, knee torque amplitude at late stance, number of steps completed while achieving a minimum swing flexion amplitude, thigh or shank sagittal plane rotational or linear acceleration, thigh or shank sagittal plane rotational speed amplitude, ground reaction force amplitude at foot strike, ground reaction force amplitude on toe in late stance, user center of mass linear acceleration, a ground interaction, a shank angle, or a joint angle.

14. The prosthetic or orthotic device of claim 1, wherein the controller mode transitions from the passive mode to the active mode based at least in part on a determined activity of a user.

15. A prosthetic or orthotic device (POD) comprising:
a first limb member;
a second limb member coupled to the first limb member at a joint;

an actuator coupled to the first limb member and the second limb member and configured to actuate the first limb member relative to the second limb member; and
a controller configured to control the actuator, the controller further configured to:
cause the actuator to exhibit a force rejection behavior during at least a portion of stance phase,
cause the actuator to exhibit a force following behavior during at least a portion of swing phase, and
based on a determination that a gait parameter satisfies a gait parameter threshold, further cause the actuator to exhibit at least one behavior of: apply a first torque at the joint to cause the POD to flex during at least a portion of stance phase, decelerate flexion of the POD during at least a first portion of the swing phase, or decelerate extension of the POD during at least a second portion of the swing phase, wherein the actuator exhibits the at least one behavior at a power level that varies in proportion with the gait parameter.

16. A prosthetic or orthotic device (POD) comprising:
a joint; and
a controller configured to:
receive gait parameter data; and
select an active mode or a passive mode based at least in part on the gait parameter data;
wherein in the passive mode, the controller causes an increase in resistance at the joint during stance phase and causes a decrease in resistance at the joint during swing phase, and
wherein in the active mode, the controller causes:
an increase in resistance at the joint during a first portion of the stance phase,
a decrease in resistance at the joint during a second portion of the stance phase,
a decrease in resistance at the joint during at least a first portion of the swing phase,
an increase in resistance at the joint to decelerate flexion of the POD during at least a second portion of the swing phase, and
an increase in resistance at a third portion of the swing phase to decelerate extension of the POD during at least a third portion of the swing phase.

17. The prosthetic or orthotic device of claim 16, wherein the POD further comprises a non-motorized actuator coupled to the joint and configured to apply torque to the joint, and wherein the controller causes an increase in resistance by increasing a resistive braking effect and causes a decrease in resistance by decreasing a resistive braking effect.

18. The prosthetic or orthotic device of claim 17, wherein the non-motorized actuator is a magnetorheological fluid actuator.

19. The prosthetic or orthotic device of claim 16, wherein the POD further comprises a motorized actuator coupled to the joint and configured to apply torque to the joint, and wherein the controller causes an increase in resistance by causing the motorized actuator to apply torque to the joint in an opposite direction of a determined torque at the joint and causes a decrease in resistance by causing the motorized actuator to apply torque to the joint in a same direction as a determined velocity of the joint.

* * * * *